(12) United States Patent
Kobayashi

(10) Patent No.: US 10,473,649 B2
(45) Date of Patent: Nov. 12, 2019

(54) FLUIDIC DEVICE, TRANSFER MEMBER, AND METHOD FOR FABRICATING FLUIDIC DEVICE

(71) Applicant: Rie Kobayashi, Shizuoka (JP)

(72) Inventor: Rie Kobayashi, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 155 days.

(21) Appl. No.: 14/916,203

(22) PCT Filed: Sep. 19, 2014

(86) PCT No.: PCT/JP2014/075766
§ 371 (c)(1),
(2) Date: Mar. 3, 2016

(87) PCT Pub. No.: WO2015/041373
PCT Pub. Date: Mar. 26, 2015

(65) Prior Publication Data
US 2017/0322202 A1    Nov. 9, 2017

(30) Foreign Application Priority Data

Sep. 19, 2013 (JP) .................................. 2013-194508
Jul. 25, 2014 (JP) .................................. 2014-151898

(51) Int. Cl.
*G01N 33/52* (2006.01)
*G01N 33/558* (2006.01)
(Continued)

(52) U.S. Cl.
CPC ......... *G01N 33/523* (2013.01); *G01N 33/558* (2013.01); *G01N 35/00029* (2013.01);
(Continued)

(58) Field of Classification Search
CPC ............... G01N 33/523; G01N 33/558; G01N 35/00029; B01L 3/5023
See application file for complete search history.

(56) References Cited

U.S. PATENT DOCUMENTS 4,774,192 A    9/1988  Terminiello et al.
5,260,222 A *  11/1993 Patel ..................... B01L 3/5023
                                                      422/412
(Continued)

FOREIGN PATENT DOCUMENTS

JP    2007-512390       5/2007
JP    2007-248073 A    9/2007
(Continued)

OTHER PUBLICATIONS

International Search Report dated Jan. 6, 2015 for counterpart International Patent Application No. PCT/JP2014/075766 filed Sep. 19, 2014.
(Continued)

*Primary Examiner* — Melanie Brown
(74) *Attorney, Agent, or Firm* — Oblon, McClelland, Maier & Neustadt, L.L.P.

(57) ABSTRACT

Provided is a fluidic device, including: a porous flow path member; an absorbent member contacting the flow path member and configured to absorb a liquid; and a barrier member covering at least a portion of the absorbent member, wherein the absorbent member contains a liquid-absorbent polymer that absorbs the liquid, and a lyophilic polymer having lyophilicity to the liquid.

16 Claims, 8 Drawing Sheets

(51) Int. Cl.
  *G01N 35/00* (2006.01)
  *B01L 3/00* (2006.01)
(52) U.S. Cl.
  CPC .. *B01L 3/5023* (2013.01); *G01N 2035/00099* (2013.01); *G01N 2035/00108* (2013.01)

(56) References Cited

U.S. PATENT DOCUMENTS

| | | | |
|---|---|---|---|
| 5,772,961 A | 6/1998 | Mico | |
| 6,258,276 B1* | 7/2001 | Mika | B01D 61/027 210/638 |
| 2002/0142291 A1* | 10/2002 | Bauer | G01N 33/54386 435/5 |
| 2005/0080182 A1 | 4/2005 | Ahmed et al. | |
| 2008/0213920 A1* | 9/2008 | Nazareth | G01N 33/558 436/536 |
| 2009/0053829 A1* | 2/2009 | Okamura | G01N 33/52 436/501 |
| 2009/0253119 A1* | 10/2009 | Zhou | G01N 33/558 435/5 |
| 2009/0298191 A1* | 12/2009 | Whitesides | G01N 33/523 436/164 |
| 2010/0233033 A1 | 9/2010 | Horiuchi et al. | |
| 2011/0189792 A1 | 8/2011 | Reinhartz et al. | |
| 2011/0236999 A1* | 9/2011 | Liotta | G01N 33/521 436/518 |
| 2013/0210991 A1* | 8/2013 | Fonnum | C08F 6/24 524/547 |
| 2014/0212960 A1* | 7/2014 | Abe | G01N 33/523 435/288.7 |
| 2016/0011188 A1* | 1/2016 | Anderberg | G01N 33/525 422/420 |

FOREIGN PATENT DOCUMENTS

| | | |
|---|---|---|
| JP | 2009-063482 | 3/2009 |
| JP | 2010-515877 | 5/2010 |
| JP | 2012-189346 * | 4/2012 |
| JP | 2012-189346 | 10/2012 |
| WO | WO 2008/001737 A1 | 1/2008 |
| WO | WO 2008/049083 A2 | 4/2008 |

OTHER PUBLICATIONS

Office Action dated Feb. 20, 2018 in Japanese Patent Application No. 2014-151898.

\* cited by examiner

FIG. 19

| Ratio of hydrophilic resin (%) | 1% | 5% | 10% | 50% |
|---|---|---|---|---|
| Enlarged image of absorbent member | | | | |
| State of voids | Continuous cell is formed | Continuous cell is formed | Independent cells start to be formed | Many voids are filled with resin |

FLUIDIC DEVICE, TRANSFER MEMBER, AND METHOD FOR FABRICATING FLUIDIC DEVICE

TECHNICAL FIELD

The present invention relates to a fluidic device provided with an absorbent member.

BACKGROUND ART

Conventionally, fluidic devices that include a porous flow path member have been used for performing various operations such as separation, mixing, analyses, etc. of liquids. A detection agent can be contained in the flow path member of the fluidic devices. Therefore, the fluidic devices can be used as, for example, biochemical sensors for blood testing or DNA testing, or chemical sensors for quality control of foods or beverages.

However, fluidic devices have a problem that if an analyte liquid stagnates in the flow path member containing a detection agent, the detection agent spreads through the flow paths and smudges detection lines, etc. to make judgment difficult. Hence, it has been known to provide a fluidic device with an absorbent member for absorbing any excess analyte liquid. As an absorbent member for a fluidic device, for example, a highly absorbent fiber that is water-swellable to 10 times as large is known (see PTL 1). As another example of an absorbent member, a member that contains an absorbent core made of highly absorbent polymer particles is known (see PTL 2).

When the absorbent member gets exposed from the fluidic device, a hand may happen to touch it and may be contaminated with an analyte such as blood that is absorbed in the absorbent member. Hence, PTL 3 discloses that a protective coating film is provided over the layer for absorbing a fluid.

CITATION LIST

Patent Literature

PTL 1 Japanese Patent Application Laid-Open (JP-A) No. 2009-63482
PTL 2 JP-A No. 2012-189346
PTL 3 JP-A No. 2010-515877

SUMMARY OF INVENTION

Technical Problem

However, when an absorbent member of a fluidic device is covered with a barrier member such as a protective coating film, pressure tends to be applied to the absorbent member by the barrier member when the absorbent member swells by absorbing a liquid. This may cause the liquid absorbed in the absorbent member to flow back, resulting in a problem that the performance of the fluidic device is spoiled.

Solution to Problem

A fluidic device of the present invention includes:
a porous flow path member;
an absorbent member contacting the flow path member and configured to absorb a liquid; and
a barrier member covering at least a portion of the absorbent member,
wherein the absorbent member contains:
a liquid-absorbent polymer that absorbs the liquid: and
a lyophilic polymer having lyophilicity to the liquid.

Advantageous Effects of Invention

As explained above, the absorbent member of the fluidic device of the present invention contains a liquid-absorbent polymer that absorbs a liquid, and a lyophilic polymer having lyophilicity to a liquid. This makes it less easy for the liquid absorbed in the absorbent member to flow back, resulting in an effect that the performance of the fluidic device can be improved.

BRIEF DESCRIPTION OF DRAWINGS

FIG. 19 shows enlarged images, captured with a digital microscope, of void structures of various absorbent members containing the hydrophilic polymer (hydrophilic resin) at different ratios.

DESCRIPTION OF EMBODIMENTS

An embodiment of the present invention will be explained below with reference to the diagrams.

<<Whole Configuration of Embodiment>>

Figure 1:
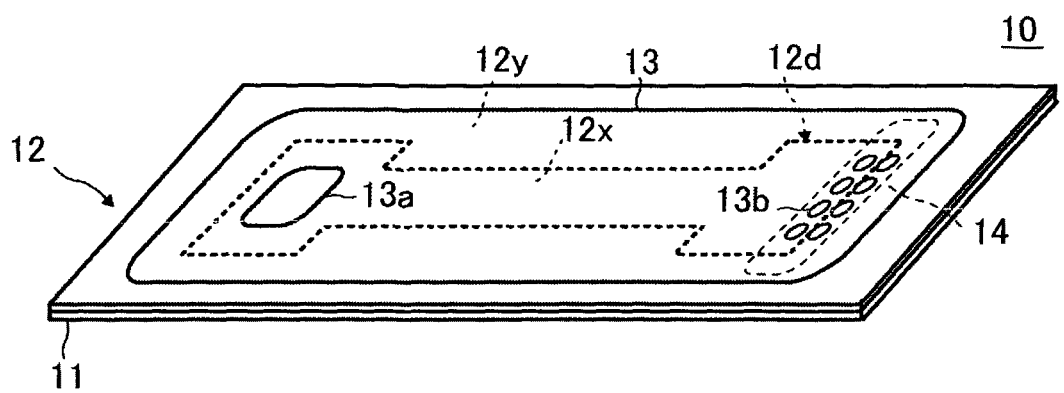
FIG. 1 is a perspective diagram of a fluidic device according to an embodiment of the present invention.
Figure 2:
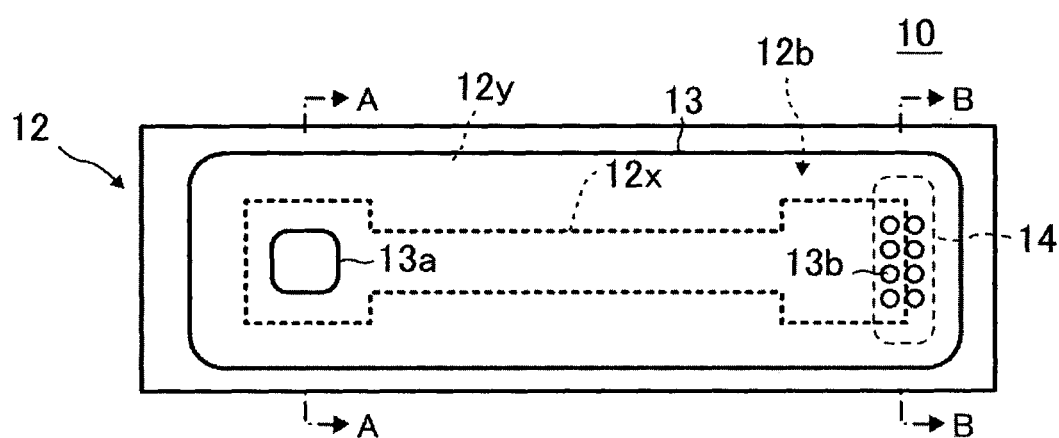
FIG. 2 is a plan view of a fluidic device according to an embodiment of the present invention.
Figure 3:
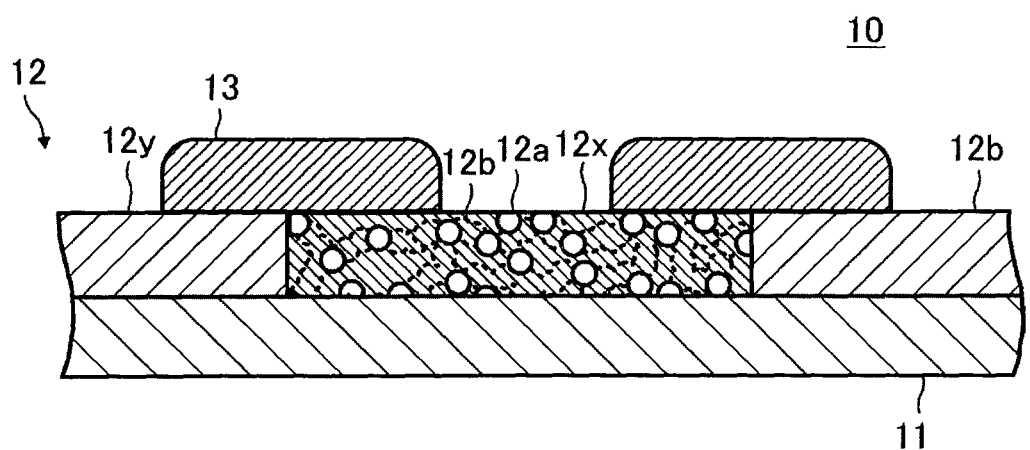
FIG. 3 is a cross-sectional diagram of a fluidic device according to an embodiment of the present invention.
Figure 4:
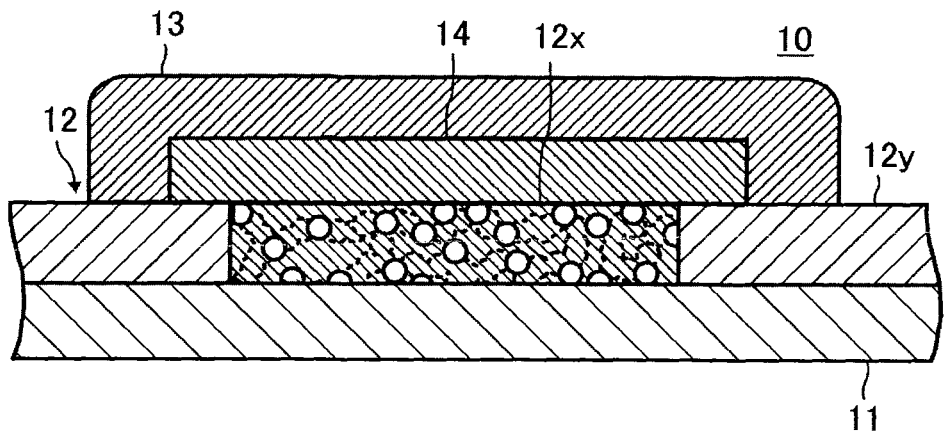
FIG. 4 is a cross-sectional diagram of a fluidic device according to an embodiment of the present invention.

First, the whole configuration of an embodiment will be explained with reference to FIG. 1 to FIG. 4. FIG. 1 is a perspective diagram of a fluidic device according to an embodiment of the present invention. FIG. 2 is a plan view of a fluidic device according to an embodiment of the present invention. FIG. 3 is a cross-sectional diagram of the fluidic device of FIG. 2 taken along a line A-A. FIG. 4 is a cross-sectional diagram of the fluidic device of FIG. 2 taken along a line B-B.

A fluidic device 10 includes a porous flow path member 12, an absorbent member 14 contacting the flow path member 12 and configured to absorb a liquid, and a barrier member 13 covering at least a portion of the absorbent member. The absorbent member 14 contains a liquid-absorbent polymer that absorbs a liquid, and a lyophilic polymer having lyophilicity to a liquid. A case where the liquid is water, the liquid-absorbent polymer is a water-absorbent polymer, and the lyophilic polymer is a hydrophilic polymer will be explained below as an embodiment of the present invention. However, the present invention is not limited to this embodiment. For example, the liquid may be an organic solvent, the liquid-absorbent polymer may have absorbability to this organic solvent, and the lyophilic polymer may be lyophilic to this organic solvent. The organic solvent is not particularly limited, and examples thereof include alcohols such as methyl alcohol, ethyl alcohol, 1-propyl alcohol, and 2-propyl alcohol, and ketones such as acetone and MEK (methyl ethyl ketone). Various publicly-known materials are used as the liquid-absorbent polymer and the lyophilic polymer with respect to an organic solvent.

In an embodiment, a contact angle between a base member and water can be used as a degree of hydrophilicity or hydrophobicity. In this case, a substance having a large contact angle can be regarded as having a high hydrophobicity. In this case, a substance having a contact angle to water of 45 degrees or less at room temperature can be regarded as hydrophilic, and a substance having a contact angle to water of 60 degrees or greater at room temperature can be regarded as hydrophobic, where the contact angles are measured based on the coordinates on a water droplet image according to an ATAN1/2θ method and a close-up method based on Young's equation, which is a contact angle measurement model used the most commonly in various fields internationally as a formula for calculating a contact angle.

<<Base Member>>

In an embodiment of the present invention, the flow path member 12 may be provided over a base member 11 as shown in FIG. 1 to FIG. 4. The base member 11 is not particularly limited, and any base member that is organic, inorganic, or metallic may be used according to the purpose. It is preferable that at least one side of the base member 11 be covered with a hydrophobic resin, although this is not limiting. When the fluidic device 10 is used as a sensor chip, the base member 11 is preferably a synthetic resin that is lightweight, flexible, and inexpensive. According to the present invention, a base member 11 having a high durability, such as a plastic sheet, can be selected. Therefore, the durability of the fluidic device will also be improved as a result.

Examples of the base member 11 include base members made of polyvinyl chloride, polyethylene terephthalate, polypropylene, polystyrene, polyvinyl acetate, polycarbonate, polyacetal, modified polyphenyl ether, polybutylene phthalate, and an ABS resin. Among these, a base member 11 made of polyethylene terephthalate is particularly preferable because it is inexpensive and versatile.

The shape of the base member 11 is not particularly limited, but a sheet shape is preferable. The average thickness of the base member 11 is not particularly limited and may be appropriately selected according to the purpose. However, it is preferably from 0.01 mm to 0:5 mm. In the present embodiment, the thickness of the measurement target may be measured with a micrometer from a total of 15 positions of the measurement target, namely 5 positions in the longer direction and 3 positions in the width direction that are defined at substantially equal intervals, and the average of the measured values may be used as the average thickness, although this is not particularly limiting. In the present embodiment, the thickness may be the length of the measurement target in the direction perpendicular to the interface at which the base member 11 and the flow path member 12 contact each other. When the average thickness is less than 0.01 mm, the base member 11 may not be able to maintain the strength enough to qualify as a base member. When the average thickness is greater than 0.5 mm, the base member may have insufficient flexibility depending on the material, and may be difficult to use as a sensor.

<<Flow Path Member>>

The flow path member 12 of the fluidic device 10 is not particularly limited, and examples thereof include a member made of a hydrophilic porous material that is partially hydrophobized to form a pattern for defining a flow path. Such a flow path member 12 includes a porous portion 12x that is not hydrophobized, and a flow path wall 12y that is hydrophobized, as shown in FIG. 3 and FIG. 4. The porous portion 12x includes pores (12a and 12b). A flow path is formed when a liquid flows through the pores (12a and 12b). In FIG. 3, a void 12a is a void formed in a cross-section of FIG. 2 taken along a line A-A. A void 12b is a void in a deeper portion in the cross-section. It is preferable that cells be present in the hydrophilic porous material, and that the cells be linked and form a continuous cell. A continuous cell is different from independent cells that are not linked. The cells forming a continuous cell have a minute pore in the wall between the cells. Therefore, the continuous cell has a function of absorbing a liquid by means of a capillary action or letting a gas pass through. The flow path member 12 delivers a liquid by utilizing a capillary action. Therefore, an external actuator such as a pump is unnecessary.

The hydrophilic porous material is not particularly limited, and an appropriate one may be selected according to the purpose. However, it is preferably a base member having hydrophilicity and a high voidage. A hydrophilic porous material is a porous material into which an aqueous solution can easily penetrate. A material can be said to be easily penetrable, when in a test for water penetrability evaluation, a plate-shaped test piece of the material is dried for 1 hour at 120° C., pure water (0.01 mL) is dropped down onto the surface of the dried test piece, and the pure water (0.01 mL) completely penetrates into the test piece within 10 minutes.

The voidage of the hydrophilic porous material is not particularly limited, and may be appropriately selected according to the purpose. However, it is preferably from 40% to 90%, and more preferably from 65% to 80%. When the voidage is greater than 90%, the hydrophilic porous material may not be able to keep the strength to qualify as a base member. When the voidage is less than 40%, the penetrability of an analyte liquid may be poor.

The voidage can be calculated according to the calculation formula 1 below, based on the basis weight (g/m²) and the thickness (μm) of the hydrophilic porous material, and the specific gravity of the component thereof.

Voidage (%)={1−[basis weight (g/m²)/thickness (μm)/specific gravity of the component]}×100 [Calculation Formula 1]

The hydrophilic porous material is not particularly limited, and an appropriate one may be selected according to the purpose. Examples thereof include filter paper, regular paper, high-quality paper, watercolor paper, Kent paper, synthetic paper, synthetic resin film, special-purpose paper having a coating, fabric, fiber product, film, inorganic substrate, and glass.

Examples of the fabric include artificial fiber such as rayon, bemberg, acetate, nylon, polyester, and vinylon, natural fiber such as cotton and silk, blended fabric of those above, or non-woven fabric of those above.

Among these, filter paper is preferable because it has a high voidage and a favorable hydrophilicity. When the fluidic device 10 is used as a biosensor, the filter paper is preferable as the stationary phase of the paper chromatography.

The shape and average thickness of the hydrophilic porous material are not particularly limited and may be appropriately selected according to the purpose. However, the hydrophilic porous material is preferably a sheet-shaped. The average thickness of the hydrophilic porous material is not particularly limited and may be appropriately selected according to the purpose. However, it is preferably from 0.01 mm to 0.3 mm. When the average thickness is less than 0.01 mm, the hydrophilic porous material may not be able to keep the strength to qualify as a base member. When the average thickness is greater than 0.3 mm, it may be less easy to form a barrier portion described later in the hydrophilic porous material.

The flow path wall 12y provided in the porous flow path member has hydrophobicity. Hydrophobicity means that the flow path wall is not eroded or destroyed by an aqueous fluid (e.g., an analyte liquid) moving through the flow path of the flow path member 12, or has a barrier property against water. A hydrophobizing method is not particularly limited. Examples thereof include a method of filling the voids of the hydrophilic porous material with, for example, a thermoplastic material, and according to necessity, further with other flow path wall forming materials such as an organic fatty acid, a long-chain alcohol, and other components appropriately selected.

It is possible to hydrophobize the hydrophilic porous material by transferring the flow path wall forming materials into the hydrophilic porous material, as will be described later. In the following explanation for each of the flow path wall forming materials such as a thermoplastic material, characteristics related with this method will also be explained, where appropriate.

< Thermoplastic Material>

A thermoplastic material for flow path wall formation is not particularly limited, and an appropriate one may be selected according to the purpose, as long as it has durability with which the structure of the fluidic device 10 is not easily collapsed when it is impregnated with water. For example, the thermoplastic material is preferably at least one selected from fat and oil, and thermoplastic resin.

—Fat and Oil—

The fat and oil means fat, fatty oil, and brazing material that are solid at normal temperature.

The fat and oil is not particularly limited, and appropriate one may be selected according to the purpose. Examples thereof include carnauba wax, paraffin wax, microcrystalline wax, paraffin oxide wax, candelilla wax, montan wax, ceresin wax, polyethylene wax, polyethylene oxide wax, castor wax, beef tallow hardened oil, lanolin, Japan tallow, sorbitan stearate, sorbitan palmitate, stearyl alcohol, polyamide wax, oleylamide, stearylamide, hydroxystearic acid, synthetic ester wax, synthetic alloy wax, and sunflower wax. One of these may be used alone, or two or more of these may be used in combination. Among these, candelilla wax and synthetic ester wax are preferable because they can easily realize formation of the flow path wall 12y.

—Thermoplastic Resin—

The thermoplastic resin is not particularly limited, and an appropriate one may be selected according to the purpose. Examples thereof include polyolefin such as polyethylene and polypropylene, and polyamide-based resin such as polyethylene glycol, polyethylene oxide, acrylic resin, polyester resin, ethylene/vinyl acetate copolymer, ethylene/acrylate copolymer, urethane resin, cellulose, vinyl chloride/vinyl acetate copolymer, petroleum resin, rosin resin, nylon, and copolymer nylon. One of these may be used alone or two or more of these may be used in combination.

Each thermoplastic material may be used as it is, but is preferably contained in the form of an emulsion together with an organic fatty acid and a long-chain alcohol. In this case, when the thermoplastic material is heated by a thermal head, separation preferentially occurs at the boundary between the particles having formed the emulsion, to break away the particles and transfer them into the surface of the hydrophilic porous base member. Therefore, the edge portions of the transferred material become sharp. Further, because the thermoplastic material emulsion is aqueous, it is advantageous in terms of having low environmental impact.

The method for forming an aqueous emulsion of the thermoplastic material is not particularly limited, and an appropriate method may be selected according to the purpose. Examples include a method of emulsifying the thermoplastic material by adding an organic fatty acid and an organic base to water and using the produced salt as an emulsifying agent.

The melting start temperature of the thermoplastic material is not particularly limited and may be appropriately selected according to the purpose. However, it is preferably from 50° C. to 150° C., and more preferably from 60° C. to 100° C. When the melting start temperature is lower than 50° C., storage stability under high-temperature conditions may be poor. When it is higher than 150° C., transferability when performing thermal transfer may be poor.

The melting start temperature of the thermoplastic material means a flowing start temperature that is observed by hardening the thermoplastic material, introducing it into a cylinder-shaped vessel having an opening with a diameter of 0.5 mm in the bottom, setting the vessel on an elevated flow tester (product name: SHIMADZU FLOW TESTER CFT-100D manufactured by Shimadzu Corporation), raising the temperature of the sample at a constant rate of 5° C./min under a load of a cylinder pressure of 980.7 kPa, and measuring the melt viscosity and flow properties of the sample due to the temperature rise.

The content of the thermoplastic material in the flow path wall forming materials is not particularly limited and may be appropriately selected according to the purpose. However, it is preferably 75% by mass or greater. When the content is less than 75% by mass, the sensitivity to heat as a transfer member may be poor.

<Organic Fatty Acid>

The organic fatty acid for flow path wall formation is not particularly limited, and an appropriate one may be selected according to the purpose. However, an organic fatty acid that has a predetermined acid value and a predetermined melting point is preferably used. The acid value of the organic fatty acid is not particularly limited and may be appropriately selected according to the purpose. However, it is preferably from 90 mgKOH/g to 200 mgKOH/g, and more preferably from 140 mgKOH/g to 200 mgKOH/g. When the acid value is less than 90 mgKOH/g, the organic fatty acid may not be able to make an emulsion of the thermoplastic material. When the acid value is greater than 200 mgKOH/g, the organic fatty acid is able to make an emulsion, but may make the emulsion creamy. Therefore, the thermoplastic material may not be prepared as a coating liquid in the production of the transfer member.

The organic fatty acid having an acid value in the range described above is not particularly limited, and an appropriate one may be selected according to the purpose. Examples thereof include oleic acid (with an acid value of 200 mgKOH/g), behenic acid (with an acid value of 160 mgKOH/g), and montanic acid (with an acid value of 132 mgKOH/g). The acid value can be measured by, for example, dissolving the sample in a mixture solvent of toluene, isopropyl alcohol, and a small amount of water, and titrating the sample with a potassium hydroxide solution.

The melting point of the organic fatty acid is not particularly limited and may be appropriately selected according to the purpose. However, it is preferably from 70° C. to 90° C. When the melting point is within the preferable value range, it is close to the melting start temperature of the thermoplastic material, which makes the sensitivity property favorable. When the melting point is lower than 70° C., the flow path wall $12y$ may be softened under high-temperature conditions such as summertime.

The organic fatty acid having a melting point in the range described above is not particularly limited, and an appropriate one may be selected according to the purpose. Examples thereof include behenic acid (with a melting point of 76° C.) and montanic acid (with a melting point of 80° C.).

The melting point can be measured by using a differential scanning calorimeter "DSC7020" (manufactured by Seiko Instruments, Inc.) and measuring the temperature at which a crystal melting endothermic peak that is to appear in a temperature raising measurement with the differential scanning calorimeter ends.

The content of the organic fatty acid is not particularly limited and may be appropriately selected according to the purpose. However, it is preferably from 1 part by mass to 6 parts by mass relative to 100 parts by mass of the thermoplastic material. When the content is less than 1 part by mass, the organic fatty acid may not be able to make the thermoplastic material an emulsion, when preparing a coating liquid used for production of the transfer member. When the content is greater than 6 parts by mass, blooming of the thermoplastic material may occur.

<Long-Chain Alcohol>

The long-chain alcohol is not particularly limited, and an appropriate one may be selected according to the purpose. However, at least any selected from a long-chain alcohol represented by General Formula (1) below and a long-chain alcohol represented by General Formula (2) below is preferable.

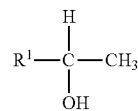

General Formula (1)

In General Formula (1), $R^1$ represents an alkyl group having 28 to 38 carbon atoms.

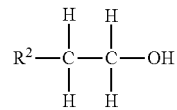

General Formula (2)

In General Formula (2), $R^2$ represents an alkyl group having 28 to 38 carbon atoms.

The long-chain alcohol is not particularly limited, and an appropriate one may be selected according to the purpose. However, it is preferably an aliphatic alcohol having a melting point of from 70° C. to 90° C. When the melting point is lower than 70° C., the flow path wall $12y$ may be softened under high-temperature conditions such as summertime. When the melting point is higher than 90° C., the transferability may be poor. When the melting point is within the preferable value range, it is close to the melting start temperature of the thermoplastic material, which makes the transferability of the transfer member favorable. The melting point can be measured by the same method for measuring the melting point of the organic fatty acid.

The long chain of the long-chain alcohol may be composed only of a straight chain, or may have branched chains. The number of carbon atoms on the long chain (the number of carbon atoms in the alkyl group) is not particularly limited and may be appropriately selected according to the purpose. However, it is preferably from 28 to 38. When the number of carbon atoms is not within the above value range, the transfer member may cause blooming along with the elapse of time, and may contaminate the surroundings when it is stored in a rolled shape.

The content of the long-chain alcohol is not particularly limited and may be appropriately selected according to the purpose. However, it is preferably from 6 parts by mass to 12 parts by mass relative to 100 parts by mass of the thermoplastic material. When the content is less than 6 parts by mass, the blooming suppression effect may not be obtained. When the content is greater than 12 parts by mass, the transferability of the transfer member may be poor when the long-chain alcohol has a temperature difference from the melting start temperature of the thermoplastic material.

<Other Components>

The other components are not particularly limited, and appropriate ones may be selected according to the purpose. Examples thereof include an organic base, a non-ionic surfactant, and a colorant.

—Organic Base—

The organic base may be used together with the organic fatty acid when emulsifying the thermoplastic material.

The organic base is not particularly limited, and an appropriate one may be selected according to the purpose. However, morpholine is preferable because it easily volatilizes after dried.

The content of the organic base is not particularly limited and may be appropriately selected according to the purpose.

However, it is preferably from 0.5 parts by mass to 5 parts by mass relative to 100 parts by mass of the thermoplastic material.

—Non-ionic Surfactant—

Addition of the non-ionic surfactant enables the aqueous emulsion of the thermoplastic material to have a small particle diameter, which improves the cohesive force of the flow path wall 12y and enables prevention of a background smear. The non-ionic surfactant is not particularly limited, and an appropriate one may be selected according to the purpose. Examples thereof include POE oleylether.

The content of the non-ionic surfactant is not particularly limited and may be appropriately selected according to the purpose. However, it is preferably from 2 parts by mass to 7 parts by mass relative to 100 parts by mass of the thermoplastic material. When the content is less than 2 parts by mass, the effect of making the particle diameter of the aqueous emulsion of the thermoplastic material small may be poor when making an aqueous emulsion of the thermoplastic material. When the content is greater than 7 parts by mass, the flow path wall 12y forming layer may become soft to degrade the friction resistance of the flow path wall 12y.

—Colorant—

The colorant may be added in order to impart the function for enabling the flow path wall 12y to be distinguished in the flow path member 12. The colorant is not particularly limited, and an appropriate one may be selected according to the purpose. Examples thereof include carbon black, azo-based pigment, phthalocyanine, quinacridone, anthraquinone, perylene, quinophthalone, aniline black, titanium oxide, zinc oxide, and chromium oxide. Among these, carbon black is preferable.

The content of the colorant is not particularly limited and may be appropriately selected according to the purpose. However, it is preferably from 0.5 parts by mass to 5 parts by mass relative to 100 parts by mass of the thermoplastic material.

The shape of the flow path wall 12y is not particularly limited and may be appropriately selected according to the purpose. Examples thereof include one of a straight line, a curve, and a junction of a plurality of branches, or combinations of these.

The pattern width of the flow path wall 12y (the width of a wall portion) is not particularly limited, and patterning may be applied with an arbitrary width according to the size of the fluidic device 10. However, the width is preferably 500 μm or greater. When the pattern width is less than 500 μm, the voids in the hydrophilic porous base member may be insufficiently filled with the hydrophobizing materials, which may make the flow path wall fail to function as a liquid-impenetrable barrier.

According to an embodiment of the present invention, the flow path wall 12y may be formed to have an arbitrary length in the direction of thickness of the hydrophilic porous material from the surface thereof into the interior thereof, i.e., in the direction of depth. Factors that control the length include the melt viscosity and the hydrophilicity of the fat and oil or the thermoplastic resin. The lower the melt viscosity, the easier it becomes for the fat and oil or the thermoplastic resin to penetrate into the interior of the hydrophilic porous material from the surface thereof, which enables a long length. Conversely, the higher the melt viscosity, the harder it becomes for the fat and oil or the thermoplastic resin to penetrate into the interior of the hydrophilic porous material from the surface thereof, which enables a substantially non-penetrated state. It is possible to control the thickness by controlling the melt viscosity.

Meanwhile, as for the hydrophilicity of the fat and oil and the thermoplastic resin, ones with a higher hydrophilicity can more easily penetrate into the interior of the hydrophilic porous material from the surface thereof, which enables a long length. Conversely, ones with a lower hydrophilicity can more hardly penetrate into the interior of the hydrophilic porous material from the surface thereof, which enables a substantially non-penetrated state. It is possible to control the thickness by controlling the hydrophilicity, but the melt viscosity influences the penetrability much more than the hydrophilicity does.

The melt viscosity of the thermoplastic material varies depending also on the hydrophilicity of the hydrophilic porous material, or the fat and oil or the thermoplastic resin. Therefore, the value range of the melt viscosity to be mentioned below does not necessarily apply, but the thermoplastic material (the fat and oil, and the thermoplastic resin), if it is used in a hydrophilic porous base member such as cellulose, can be freely and arbitrarily selected from materials of a very broad viscosity range of from 3 mPa·s to 1,600 mPa·s, and can be thermally transferred. In particular, in order to make the flow path wall forming materials penetrate into the interior of the hydrophilic porous material from the surface thereof so as to make the length of the flow path wall in the direction of thickness large, it is preferable to use a thermoplastic material having a melt viscosity of from 6 mPa·s to 200 mPa·s.

Meanwhile, conventional techniques for flow path wall formation include an inkjet system. For example, an inkjet printer using an ultraviolet curable resin ink discharges the ink from the head and makes the ink droplets fly and land into a porous layer. Therefore, there is a limitation; in order for a liquid to be discharged from the head, the viscosity of the liquid needs to be as low as 15 mPa·s at the maximum, or needs actually to be lower than 10 mPa·s, or otherwise the liquid cannot be discharged from the head, which allows poor latitude in the selection of the material. For this reason, the ink that can be used in the inkjet printer has a very low viscosity, and hence easily spreads in a porous layer, making a large bleed.

The same can be said for a wax printer. A wax printer thermally melts a solid ink and discharges the ink from the head to make droplets of the melted ink fly and land into a porous layer. Therefore, there is the same viscosity limitation as described above, in order for the ink to be discharged from the head, resulting in a poor latitude for the material. Besides, in the case of a wax printer, in reality, the temperature of the solid ink lowers during the flight to thereby make the viscosity have already risen above the level at which the ink can penetrate into the porous layer when the ink droplets land on the porous layer. Therefore, the ink droplets stop on the surface of the porous layer and cannot penetrate into the interior of the porous layer. This indispensably necessitates a step of heating the porous layer to a temperature at which the thermoplastic material can melt sufficiently in order to make the material penetrate. Therefore, not only does the process become complicated, but the porous layer cannot avoid being entirely heated, which makes it easier for the ink to spread also in the horizontal direction, making a large bleed.

In contrast, the thermal transfer system performs printing by bringing the thermal head into direct contact with a porous layer via the transfer member for flow path wall formation. Therefore, the thermal head applies heat only locally to a minute portion to which to transfer the ink, which enables effective suppression of the spreading of the thermoplastic material in the horizontal direction, resulting in a highly linear flow path with no bleed.

The length can also be controlled by controlling the energy to be applied for thermal compression bonding. That is, the more the energy to be applied is increased to raise the temperature of the fat and oil, and the thermoplastic resin, which are the thermoplastic material, the more inward they penetrate, whereas the more the temperature is lowered, the closer to the surface they stop.

In order to make an analyte liquid stay within a predetermined region for a specific mixing and a specific reaction, a portion of the porous portion 12x of the flow path member 12 may be provided with a larger width as a reaction field. A detection agent to be placed in the reaction field is not particularly limited as long as it can detect a predetermined analyte contained in the analyte liquid. Examples thereof include a reagent that changes colors due to various antigen-antibody reactions, a pH indicator, various ionophores that change colors by reacting with various ions such as a lead ion, a copper ion, and a nitrite ion, and a reagent that changes colors by reacting with various agricultural chemicals.

<<Absorbent Member>>

Fiber has been used as an absorbent member in the conventional fluidic devices. Fiber is excellent in a rapid water absorptivity. However, when pressure is applied to the absorbent member by a barrier member such as a protective coating film when the absorbent member swells by absorbing water, it can be considered that the absorbed water, which is merely retained in the voids between the fiber filaments, may tend to flow back into the flow path through the voids in the fiber filaments. In contrast, the absorbent member 14 of the present embodiment contains a water-absorbent polymer that can absorb water, and a hydrophilic polymer having hydrophilicity. Therefore, since the absorbent member 14 of the present embodiment absorbs water by a mechanism different from the water absorbing mechanism of the fiber, it can be considered that even when it has pressure applied by the barrier member 13, it is less likely for the water to flow back, because the water is retained by the water-absorbent polymer and the hydrophilic polymer.

In addition, the absorbent member 14 of the present embodiment has a very high water absorptivity per unit mass, and the water-absorbent polymer has a characteristic of embracing water and not letting go of the water once it absorbs the water. Therefore, even after the flow path member 12 becomes dried, the water-absorbent polymer keeps retaining the water inside, and can prevent the water from flowing back into the flow path member 12. Therefore, it is less likely for a color reaction line to be smudged due to flow back of the water.

As embodiments of absorbent members, an absorbent member in which voids are formed, and an absorbent member in which a water-absorbent polymer is dispersed in a hydrophilic polymer will be explained.

When an absorbent member is required to have a high water absorptive capacity such as when the liquid to be absorbed is saline, it is preferable that the water-absorbent polymer be conjugated by the hydrophilic polymer in the absorbent member, and that voids be formed in the absorbent member. In this case, it is preferable that the voids formed in the absorbent member be continuous, that is, that the absorbent member have a continuous cell. With voids formed in the absorbent member, and with the voids preferably being continuous, the amount of liquid that will come into direct contact with the water-absorbent polymer becomes drastically large, and the amount of water to be absorbed by the absorbent member also becomes large by means of a capillary action. This can realize an absorbent member that has a good penetrability and a rapid water absorptivity.

When an absorbent member in which voids are formed is used, the voidage thereof is not particularly limited but is preferably from 30% to 85%. When the voidage is less than 30%, with the insufficient voids, the ability to convey water into the interior of the absorbent member may be poor. When the voidage is greater than 85%, a sufficient water absorptivity may not be obtained because the amount of the water-absorbent polymer is relatively short.

In order for the water absorption speed to be kept high when an absorbent member in which voids are formed is used, it is preferable that the voids be maintained without the hydrophilic polymer getting dissolved in an analyte liquid during absorption thereof. Without this, it is possible to make the water come into contact with the surface of the water-absorbent polymer more rapidly, and hence the water-absorbent polymer can keep on directly absorbing water more rapidly. As a hydrophilic polymer for this purpose, it is preferable to use a water-insoluble polymer, i.e., a polymer that does not substantially dissolve in water. For the practical purpose, the water-insoluble polymer may have a solubility that justifies saying that the polymer is insoluble in water, e.g., a solubility at which when the polymer is immersed in water of 23° C. for 120 minutes, the mass of the polymer decreases by 0.5% or less.

When an absorbent member in which voids are formed is used, the ratio of the hydrophilic polymer, e.g., a water-insoluble hydrophilic polymer in the absorbent member is preferably from 1% by mass to 60% by mass on a mass fraction basis, and particularly, in order to raise the water absorption speed, from 1% by mass to 10% by mass. When the ratio of the hydrophilic polymer is less than 1% by mass, the function of the hydrophilic polymer to conjugate the water-absorbent polymer may be poor, and the absorbent member may not be able to maintain the structure. When the ratio of the hydrophilic polymer is greater than 60% by mass, the amount of the water-absorbent polymer is relatively short, which may make it impossible to obtain a sufficient water absorptive capacity. When the ratio of the hydrophilic polymer is greater than 10% by mass, the voids may be formed as independent cells, or a sufficient amount of voids may not be obtained, which may make it impossible to obtain a sufficient water absorption speed. However, the ratio is not particularly limited to the above preferable ranges because preferable ranges are also dependent on the kind of the hydrophilic polymer.

FIG. 19 shows enlarged images, captured with a digital microscope, of void structures of various absorbent members containing the hydrophilic polymer (hydrophilic resin) at different ratios. In the absorbent members of FIG. 19, the water-absorbent polymer is AQUAKEEP (10SH-NF manufactured by Sumitomo Seika Chemicals Co., Ltd.), and the hydrophilic polymer is polyvinyl butyral (ESLEC BX-1 manufactured by Sekisui Chemical Co., Ltd.).

Further, in a viewpoint of shortening the test time in consideration of a practical purpose, an absorbent member having a high water absorption speed is preferable with a view to accelerating the flow of an analyte liquid. On the other hand, in a viewpoint of enhancing the detection sensitivity, an absorbent member having a low water absorption speed is preferable with a view to delaying the flow of an analyte liquid to ensure a reaction time for a reagent. Furthermore, an absorbent member having a greater water absorptive capacity has a better performance as an absorbent member, and with a view to suppressing flow back of water, an absorbent member that has a high water retention after water absorption and does not release water easily is required. That is, in a practical sense, it is required to control the water absorption speed and the water retention optimally depending on the purpose. With the above-described absorbent member in which voids are formed, it is possible to control the water absorption speed to a more optimum range by using two control factors, namely, control of the water absorption speed of the water-absorbent polymer itself, and control of the water absorption speed based on a capillary action through the voids.

According to another embodiment, the water-absorbent polymer may be dispersed in the hydrophilic polymer in the absorbent member, in order for the water-absorbent polymer to be prevented from peeling or dropping off from the flow path member and the absorbent member 14. When an absorbent member in which the water-absorbent polymer is dispersed in the hydrophilic polymer is used, it is preferable to use a water-soluble polymer as the hydrophilic polymer. When a water-soluble polymer is used as the hydrophilic polymer, new voids may be formed when the water-soluble polymer gets dissolved in the water contained in an analyte liquid, which makes it possible for the water to flow more rapidly by means of a capillary action. A water-soluble polymer shows solubility to water, and contains water. However, a water-soluble polymer has a less water absorption capacity and a less water retention than those of the water-absorbent polymer. Therefore, a water-soluble polymer functions as a binder to fix the water-absorbent polymer.

Next, the water-absorbent polymer and the hydrophilic polymer constituting the absorbent member in which voids are formed and the absorbent member in which the water-absorbent polymer is dispersed in the hydrophilic polymer will be explained.

The water-absorbent polymer is not particularly limited, as long as it is a polymer that can absorb water. Examples thereof include a polymeric compound having a carboxyl group or a salt thereof, a partially cross-linked product of a polymeric compound having a carboxyl group or a salt thereof, and a partially cross-linked product of a polysaccharide.

Examples of the polymeric compound having a carboxyl group or a salt thereof include sodium polyacrylate. Polymers described as "highly water-absorbent polymers" in JP-A No. 2012-189346 can also be raised as examples of the water-absorbent polymer. This publication can be incorporated herein by reference.

Examples of the partially cross-linked product of a polymeric compound having a carboxyl group or a salt thereof include a cross-linked polyacrylic acid salt, a cross-linked vinyl alcohol/acrylic acid salt copolymer, and cross-linked polyvinyl alcohol/polymaleic anhydride salt graft copolymer.

Examples of the partially cross-linked product of a polysaccharide include a cross-linked carboxymethyl cellulose salt, and a cross-linked starch/acrylic acid salt graft copolymer.

Among these, sodium polyacrylate is preferable because it has a high water absorptivity, and has a high water retention ability and does not release water after it absorbs water. Specific examples of sodium polyacrylate include AQUAKEEP SERIES manufactured by Sumitomo Seika Chemicals, Co., Ltd.

On the other hand, the water-absorbent polymer can take in water from the polymer surface, and store a lot of water in the web structure of the cross-linkage in the polymer. Therefore, it has a high absorptivity to water. The shape of the water-absorbent polymer is not particularly limited. However, it is preferable that the water-absorbent polymer have a particle shape, in order to have as large a surface area as possible to enhance the water absorptivity. In this case, the volume basis average particle diameter of the particles is preferably 60 µm or less, more preferably 45 µm or less, and still more preferably 30 µm or less. When the volume basis average particle diameter is greater than 60 µm, it becomes necessary to make the thickness of the absorbent member 14 equal to or greater than, for example, 120 µm, which may make it difficult to form the absorbent member 14 by transfer. The volume basis average particle diameter of the particles means the average of particle diameters when a particle size distribution is plotted based on volume percent. The method for measuring the volume basis average particle diameter of the particles may be a measuring method using an aero track LDSA-SPR3500A (manufactured by Nikkiso Co., Ltd.) combined with a particle size distribution measuring instrument capable of performing dry measurement, e.g., a dry disperser PD-10S (manufactured by Nikkiso Co., Ltd.). The particles to be measured are made into an aerosol state with PD-10S, and introduced into the measurement cell of the LDSA-SPR3500A equipment. Then, 20,000 particles are detected with a laser diffraction method, and the average of the volume basis particle diameters of the measured particles is calculated with arithmetic operation software included in the equipment.

The hydrophilic polymer is not particularly limited, and an appropriate one may be selected according to the purpose. Examples thereof include poly(ethylene oxide), polyvinyl alcohol, polyvinyl pyrrolidone, polyacrylic acid, polyhydroxyethyl, polyacrylamide, polyethylene glycol, polyethylene oxide, polyamide, polyvinyl sulfonic acid, polystyrene sulfonic acid, polyacrylamide sulfonic acid, and a butyral resin.

Among these, a butyral resin is preferable as a water-insoluble hydrophilic polymer because it is excellent in a film forming property and adhesiveness. Specific examples of a butyral resin include ESLEC SERIES manufactured by Sekisui Chemical Co., Ltd. Further, poly(ethylene oxide), polyvinyl pyrrolidone, and polyacrylic acid are preferable as a water-soluble hydrophilic polymer. Specific examples of poly(ethylene oxide) include ALKOX (Registered Trademark) SERIES manufactured by Meisei Chemical Works, Ltd.

When forming the absorbent member 14 over the flow path member 12 by transfer, it is preferable that the hydrophilic polymer be a thermoplastic material. However, when the ratio of the hydrophilic polymer to the water-absorbent polymer is small, the hydrophilic polymer may be any other material than a thermoplastic material.

<<Barrier Member>>

In the present embodiment, the barrier member 13 is in contact with the flow path wall 12y of the flow path member 12 and the absorbent member 14, and covers at least a portion of the absorbent member 14. The barrier member 13 has a barrier property against water, and preferably has a gas barrier property. Having a gas barrier property means that the barrier member has a smaller gas permeability than that of at least paper. Preferable examples of the constituent material of the barrier member 13 include materials such as a film and a laminate that have a water gas permeability (water vapor permeability) of 100 g/(m$^2$·day) or less, preferably 50 g/(m$^2$·day) or less, and more preferably 10 g/(m$^2$·day) or less, where the water gas permeability is measured according to ISO15106-1. Examples of materials having a water gas permeability of 5 g/(m$^2$·day) include a polyethylene wax, a polypropylene wax, a silicone resin, polycarbonate, and polystyrene.

The thickness of the barrier member 13 is not particularly limited, and may be appropriately selected according to the purpose. However, it is preferably from 5 μm to 100 μm, and more preferably from 10 μm to 70 μm. When the thickness is less than 5 the barrier member may not be able to have a sufficient gas shielding property to thereby promote drying over time. When the thickness is greater than 100 μm, the barrier member may have a poor adhesiveness with respect to the flow path member.

Use of the barrier member 13 in this way prevents a hand from being contaminated when touching the fluidic device 10. Therefore, the fluidic device needs not be housed.

A material preferable as the material of the barrier member 13 is not particularly limited, and an appropriate material may be selected according to the purpose. Examples thereof include waxes such a candelilla wax, polyamides such as nylon, and resins such as an ethylene/vinyl alcohol copolymer resin (EVOH) and a polyvinylidene chloride resin. These materials have thermoplasticity, and are preferable in thermal transferability, a film forming property, or the like.

The same thermoplastic materials as the flow path wall forming materials to be described later may be used as these materials. Among these, the waxes such as a candelilla wax are preferable in terms of releasability during thermal transfer. Note that resins are preferable when a gas barrier property is required.

The barrier member 13 may be an elastomer. An elastomer has elasticity, and can conform to the absorbent member 14 when it swells by absorbing water. The elongation rate of the barrier member 13 is not particularly limited, but is preferably 3% or greater, and more preferably 5% or greater. The elongation rate can be measured by performing a tensile test according to ISO527-1 with a dynamic extensometer.

In the present embodiment, an opening 13a from which to drop an analyte liquid is formed in the barrier member 13. In order to prevent the flow path from absorbing moisture during storage of the fluidic device 10, the opening 13a may be sealed with a publicly-known seal member. Examples of such a seal member include a PVC (polyvinyl chloride) film containing a water-soluble acrylic resin in its adhesive layer, an example of which is FILMOLUX 609 (with a thickness of 70 μm) manufactured by Filmolux Co., Ltd. For example, when the whole of the fluidic device 10 is hermetically sealed for storage, a seal member may not need to be provided.

An opening 13b through which the pressure in the flow path escapes into the atmospheric pressure is also formed in a portion of the barrier member 13 above the absorbent member 14. This enables the analyte liquid to penetrate into the flow path by means of a capillary action. It is preferable that the opening 13b include a plurality of holes having a diameter of about 2 mm, in order to prevent a hand from being contaminated when the hand directly touches the absorbent member that has absorbed a liquid. In order to prevent the flow path from absorbing moisture during storage of the fluidic device 10, the opening 13b may be sealed with a publicly-known seal member. The same seal member as that described above is used as this seal member. For example, when the whole of the fluidic device 10 is hermetically sealed for storage, a seal member may not need to be provided.

<<Transfer Member for Flow Path Wall Formation>>

Figure 5:
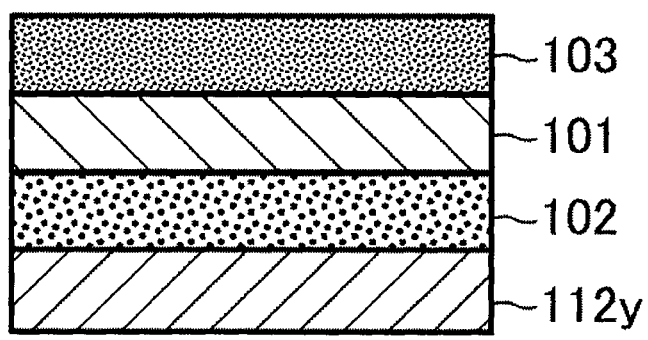
FIG. 5 is a cross-sectional diagram of a transfer member for flow path wall formation according to an embodiment of the present invention.

Next, a method for forming the flow path member 12 by transferring the flow path wall forming materials into the hydrophilic porous material will be explained. First, the transfer member for flow path wall formation will be explained with reference to FIG. 5. FIG. 5 is a cross-sectional diagram of the transfer member for flow path wall formation. The transfer member for flow path wall formation 100 is obtained by stacking a releasing layer 102 and a flow path wall forming layer 112y in this order over a support member 101, includes other layers according to necessity.

<Support Member>

The shape, structure, size, material, etc. of the support member 101 are not particularly limited, and may be appropriately selected according to the purpose. The structure may be a single-layer structure, or may be a layered structure. The size of the support member may be appropriately selected according to the size of the fluidic device 10, etc.

The material of the support member 101 is not particularly limited, and may be appropriately selected according to the purpose. Examples thereof include polyester such as polyethylene terephthalate (PET) and polyethylene naphthalene (PEN), polycarbonate, a polyimide resin (PI), polyamide, polyethylene, polypropylene, polyvinyl chloride, polyvinylidene chloride, polystyrene, a styrene/acrylonitrile copolymer, and cellulose acetate One of these may be used alone, or two or more of these may be used in combination. Among these, polyethylene terephthalate (PET) and polyethylene naphthalate (PEN) are particularly preferable.

It is preferable to perform a surface activation treatment on the surface of the support member 101, in order to improve close adhesiveness with respect to the layer to be provided over the support member 101. Examples of the surface activation treatment include a glow discharge treatment, and a corona discharge treatment.

The support member 101 may be kept after having transferred the flow path wall forming layer 112y into the hydrophilic porous material. Alternatively, the support member 101 may be peeled and removed by means of the releasing layer 102, after having transferred the flow path wall forming layer 112y.

The support member 101 is not particularly limited, and may be an appropriately synthesized product or may be a commercially available product.

The average thickness of the support member 101 is not particularly limited, and may be appropriately selected according to the purpose. However, it is preferably from 3 μm to 50 μm.

<Releasing Layer>

The releasing layer 102 has a function of improving separability between the support member 101 and the flow path wall forming layer 112y during transfer. The releasing layer 102 also has a function of thermally melting to a low viscosity liquid when heated with a heating/pressurizing unit such as a thermal head to thereby make it easier for the flow path wall forming layer 112y to be separated at the interface between the heated portion and a non-heated portion. The releasing layer 102 contains a wax and a binder resin, and further contains other components appropriately selected according to necessity.

—Wax—

The wax is not particularly limited, and an appropriate one may be selected according to the purpose. Examples thereof include: natural wax such as beeswax, carnauba wax, spermaceti, Japan tallow, candelilla wax, rice wax, and montan wax; synthetic wax such as paraffin wax, microcrystalline wax, oxide wax, ozokerite, ceresin, ester wax, polyethylene wax, and polyethylene oxide wax; higher fatty acid such as margaric acid, lauric acid, myristic acid, palmitic acid, stearic acid, furoic acid, and behenic acid; higher alcohol such as stearin alcohol and behenyl alcohol; esters such as sorbitan fatty acid ester; and amides such as stearamide and oleic amide. One of these may be used alone or two or more of these may be used in combination. Among these, carnauba wax and polyethylene wax are preferable because they are excellent in releasability.

—Binder Resin—

The binder resin is not particularly limited, and appropriate one may be selected according to the purpose. Examples thereof include an ethylene/vinyl acetate copolymer, a partially saponified ethylene/vinyl acetate copolymer, an ethylene/vinyl alcohol copolymer, an ethylene/sodium methacrylate copolymer, polyamide, polyester, polyurethane, polyvinyl alcohol, methyl cellulose, carboxymethyl cellulose, starch, polyacrylic acid, an isobutylene/maleic acid copolymer, a styrene/maleic acid copolymer, polyacrylamide, polyvinyl acetal, polyvinyl chloride, polyvinylidene chloride, an isoprene rubber, a styrene/butadiene copolymer, an ethylene/propylene copolymer, a butyl rubber, and an acrylonitrile/butadiene copolymer. One of these may be used alone, or two or more of these may be used in combination.

The method for forming the releasing layer 102 is not particularly limited, and an appropriate method may be selected according to the purpose. Examples thereof include a hot-melt coating method, and a coating method using a coating liquid obtained by dispersing the wax and the binder resin in a solvent. The average thickness of the releasing layer 102 is not particularly limited and may be appropriately selected according to the purpose. However, it is preferably from 0.5 µm to 2.0 µm. The amount of deposition of the releasing layer 102 is not particularly limited and may be appropriately selected according to the purpose. However, it is preferably from 0.5 g/m$^2$ to 8 g/m$^2$, and more preferably from 1 g/m$^2$ to 5 g/m$^2$.

<Flow Path Wall Forming Layer>

The materials, etc. of the flow path wall forming layer 112$y$ are as described above as for the flow path wall forming materials.

The method for forming the flow path wall forming layer 112$y$ is not particularly limited, and an appropriate method may be selected according to the purpose. For example, as a hot-melt coating method or a coating method using a coating liquid obtained by dispersing the thermoplastic material in a solvent, a common coating method using a gravure coater, a wire bar coater, a roll coater, or the like may be used. According to such a method, the support member 101 or the releasing layer 102 is coated with the flow path wall forming layer coating liquid. When the liquid is dried, the flow path wall forming layer is formed.

The average thickness of the flow path wall forming layer 112$y$ is not particularly limited and may be appropriately selected according to the purpose. However, it is preferably from 5 µm to 250 µm. When the average thickness is less than 5 µm, the amount of the flow path wall forming layer 112$y$ may be insufficient for filling the voids in the hydrophilic porous material. When the average thickness is greater than 250 µm, it becomes harder for heat from the thermal head to be conducted through the flow path wall forming layer 112$y$, to thereby degrade the transferability.

The amount of deposition of the flow path wall forming layer 112$y$ is not particularly limited and may be appropriately selected according to the purpose. However, it is preferably from 5 g/m$^2$ to 250.0 g/m$^2$, and more preferably from 30 g/m$^2$ to 150.0 g/m$^2$.

<Other Layers and Members>

The other layers and members are not particularly limited, and appropriate ones may be selected according to the purpose. Examples thereof include a back layer 103, an undercoat layer, and a protection film.

—Back Layer—

The transfer member for flow path wall formation 100 preferably includes a back layer 103 over a side of the support member 101 opposite to the side thereof over which the flow path wall forming layer 112$y$ is formed. Heat is directly applied to this opposite side by a thermal head or the like at a position corresponding to the shape of the flow path wall. Therefore, the back layer 103 preferably has resistance to high heat and resistance to friction with a thermal head or the like. The back layer 103 contains a binder resin, and further contains other components according to necessity.

The binder resin is not particularly limited, and an appropriate one may be selected according to the purpose. Examples thereof include a silicone-modified urethane resin, a silicone-modified acrylic resin, a silicone resin, a silicone rubber, a fluororesin, a polyimide resin, an epoxy resin, a phenol resin, a melamine resin, and nitrocellulose. One of these may be used alone or two or more of these may be used in combination.

The other components are not particularly limited, and appropriate ones may be selected according to the purpose. Examples thereof include inorganic particles of talc, silica, organopolysiloxane, etc., and a lubricant.

The method for forming the back layer 103 is not particularly limited, and an appropriate method may be selected according to the purpose. Examples thereof include common coating methods using a gravure coater, a wire bar coater, a roll coater, etc. The average thickness of the back layer 103 is not particularly limited and may be appropriately selected according to the purpose. However, it is preferably from 0.01 µm to 1.0 µm.

—Undercoat Layer—

An undercoat layer may be provided between the support member 101 and the flow path wall forming layer 112$y$, or between the releasing layer 102 and the flow path wall forming layer 112$y$. The undercoat layer contains a resin, and further contains other components according to necessity. The resin is not particularly limited, and an appropriate one may be selected according to the purpose. The resin may be any of the resins usable for the flow path wall forming layer 112$y$ and the releasing layer 102.

—Protection Film—

It is preferable to provide a protection film over the flow path wall forming layer 112$y$ for protecting the layer from contamination or damages during storage. The material of the protection film is not particularly limited, and an appropriate one may be selected according to the purpose, as long as it can be easily separated from the flow path wall forming layer 112$y$. Examples thereof include silicone sheet, polyolefin sheet such as polypropylene sheet, and polytetrafluoroethylene sheet. The average thickness of the protection film is not particularly limited and may be appropriately selected according to the purpose. However, it is preferably from 5 µm to 100 µm, and more preferably from 10 µm to 30 µm.

<Transfer of Flow Path Wall Forming Layer>

In the formation of the flow path wall 12$y$, the hydrophilic porous material and the flow path wall forming layer 112$y$ of the transfer member for flow path wall formation 100 are faced and overlapped with each other, and the flow path wall forming layer is thermally transferred. The method for thermally transferring the flow path wall forming layer 112$y$ is not particularly limited, and an appropriate method may be selected according to the purpose. Examples thereof include a method of melting and transferring the flow path wall forming layer 112y by thermal compression bonding with a serial thermal head, a line thermal head, etc. The energy applied in the thermal compression bonding is not particularly limited, and may be appropriately selected according to the purpose. However, it is preferably from 0.1 mJ/dot to 1.00 mJ/dot. When the applied energy is lower than 0.1 mJ/dot, the flow path wall forming layer 112y may be melted insufficiently. When the applied energy is higher than 1.00 mJ/dot, portions of the transfer member for flow path wall formation 100 other than the flow path wall forming layer 112y may be melted and contaminate the thermal head.

<<Transfer Member for Absorbent Member and Barrier Member Formation>>

Figure 6:
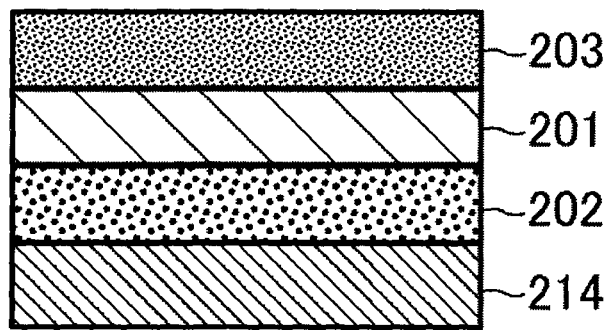
FIG. 6 is a cross-sectional diagram of a transfer member according to an embodiment of the present invention.

Next, a method for forming the absorbent member 14 and the barrier member 13 by transferring absorbent member forming materials and barrier member forming materials onto the flow path member 12 in which the flow path wall 12y has been formed. First, a transfer member for formation of the absorbent member 14 and the barrier member 13 will be explained with reference to FIG. 6. FIG. 6 is a cross-sectional diagram of a transfer member according to an embodiment of the present invention. The transfer member 200 is a transfer member for fabrication of the fluidic device 10, and includes a support member 201, a releasing layer 202 stacked over the support member 201, and an absorbent member forming layer 214 stacked over the releasing layer 202 and containing a water-absorbent polymer and a hydrophilic polymer. The absorbent member forming layer 214 contains a thermoplastic material. The transfer member 200 further includes other layers such as a back layer 203, etc. according to necessity.

After the transfer member 200 is transferred onto the flow path member 12, the releasing layer 202 need not be peeled from the absorbent member forming layer 214, but may be left over the absorbent member forming layer 214. In this case, in the fluidic device 10, the releasing layer 202 is kept remaining over the absorbent member 14 formed by the absorbent member forming layer 214. The releasing layer 202 left over the absorbent member 14 is used as the barrier member 13.

<Support Member, Releasing Layer, and Other Layers and Members>

As the support member 201, the same material as the support member 101 of the transfer member for flow path wall formation 100 is used. Therefore, a detailed explanation thereof will not be provided. As the releasing layer 202, the same material as the releasing layer 102 of the transfer member for flow path wall formation 100 is used. Therefore, a detailed explanation thereof will not be provided. As the back layer 203, etc. and the other layers and members, the same materials as the back layer 103, etc. and the other layers and members of the transfer member for flow path wall formation 100 are used. Therefore, a detailed explanation thereof will not be provided.

<Absorbent Member Forming Layer>

The material, etc. of the absorbent member forming layer 214 are just as described above as for the material, etc. of the absorbent member 14. The method for forming the absorbent member forming layer 214 is not particularly limited, and an appropriate method may be selected according to the purpose. For example, as a hot-melt coating method or a coating method using a coating liquid obtained by dispersing materials including the water-absorbent polymer, the hydrophilic polymer, etc. in a solvent, a common coating method using a gravure coater, a wire bar coater, a roll coater, or the like may be used. According to such a method, the releasing layer 202 is coated with an absorbent member formation coating liquid. When the liquid is dried, the absorbent member forming layer is formed.

The average thickness of the absorbent member forming layer 214 is not particularly limited, and may be appropriately selected according to the purpose. However, it is preferably from 15 µm to 120 µm. When the average thickness is less than 15 µm, a sufficient water absorptivity may not be obtained. When the average thickness is greater than 120 µm, it becomes harder for heat from the thermal head to be conducted through the absorbent member forming layer 214, to thereby degrade the transferability. For example, when an analyte liquid to be absorbed is saline (0.05 cc), the absorbent member needs to have a thickness of 15 µm in order to absorb the analyte liquid sufficiently, provided that the area of the absorbent member is 1 $cm^2$.

The amount of deposition of the absorbent member forming layer 214 is not particularly limited and may be appropriately selected according to the purpose. However, it is preferably from 30 $g/m^2$ to 120.0 $g/m^2$.

<Transfer of Absorbent Member Forming Layer and Barrier Member Forming Layer>

In the formation of the absorbent member forming layer 214, the absorbent member forming layer 214 of the transfer member 200 and the flow path member 12 are brought into contact with each other by being faced and overlapped with each other, and heat and pressure are applied to the transfer member 200 to transfer the absorbent member forming layer 214 onto the flow path member 12.

The absorbent member forming layer and the barrier member forming layer may be formed on separate transfer members, and may be transferred separately.

The thermal transfer method is not particularly limited, and an appropriate method may be selected according to the purpose. Examples thereof include a method of melting and transferring the absorbent member forming layer 214 by thermal compression bonding with a serial thermal head, a line thermal head, etc. The energy applied in the thermal compression bonding is not particularly limited, and may be appropriately selected according to the purpose. However, it is preferably from 0.1 mJ/dot to 1.00 mJ/dot.

When the applied energy is lower than 0.1 mJ/dot, the absorbent member forming layer 214 may be melted insufficiently. When the applied energy is higher than 1.00 mJ/dot, portions of the transfer member 200 other than the absorbent member forming layer 214 may be melted and contaminate the thermal head.

<<< Use Applications of Fluidic Devices >>>

The use applications of the fluidic device 10 are not particularly limited, and appropriate applications may be selected according to the purpose. Examples thereof include a biochemical sensor (a sensing chip) for blood testing and DNA testing, a small-size analytical device (a chemical sensor) for quality control for foods and beverages, and various microfluidic devices.

A sample (analyte) used for biochemical testing is not particularly limited, and an appropriate one may be selected according to the purpose. Examples thereof include a pathogen such as a bacterium and a virus, blood, saliva, a lesional tissue, etc. separated from living organisms, and egestion such as enteruria. Further, for performing a prenatal diagnosis, the sample may be a part of a fetus cell in an amniotic fluid, or of a dividing egg cell in a test tube. Furthermore, these samples may be, after condensed to a sediment directly or by centrifugation or the like according to necessity, subjected to a pre-treatment for cell destruction through an enzymatic treatment, a thermal treatment, a surfactant treatment, and an ultrasonic treatment, any combinations of these, etc.

The fluidic device of the present embodiment also has a function of performing chromatography (separation and refinement) of an analyte liquid, because the porous portion 12 serves as a stationary phase. In this case, the porous portion 12x having a continuous cell of which internal wall has hydrophilicity serves as the stationary phase (a carrier). Different components in the analyte liquid flow through the flow paths at different speeds because of difference in their interactions with the stationary phase during the process of their penetration through the fluid paths, i.e., difference in whether they are hydrophilic or hydrophobic.

A component having a higher hydrophilicity is more likely to adsorb to the porous portion 12x serving as the stationary phase, and repeats adsorbing and desorbing more times. Therefore, such a component penetrates through the fluid paths at a lower speed. Conversely, a component having a higher hydrophobicity penetrates without adsorbing to the stationary phase. Therefore, such a component moves rapidly through the fluid paths. By utilizing the difference in the moving speed in the analyte liquid, and extracting the target component in the analyte liquid selectively and allowing it to undergo a reaction, it is possible to use the fluidic device 10 as a highly functional chemical or biochemical sensor.

<<<Supplemental to Embodiment>>>

Figure 7:
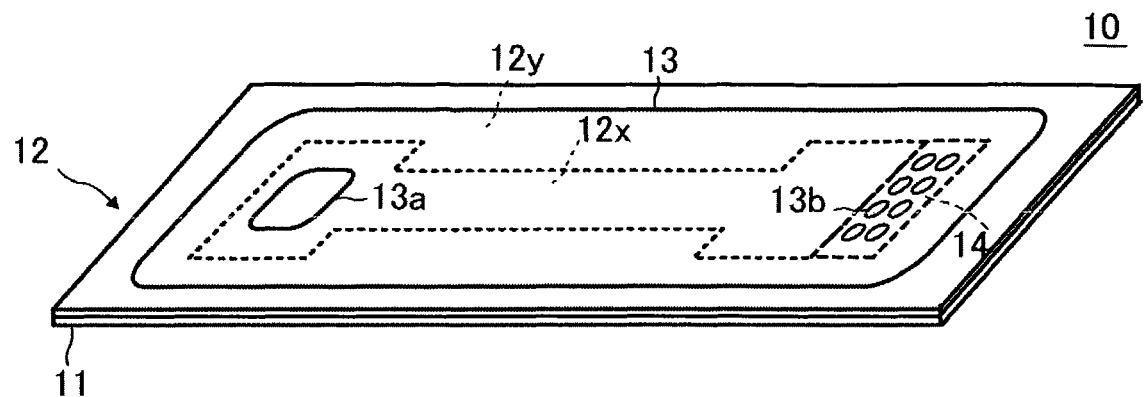
FIG. 7 is a perspective diagram of a fluidic device according to an embodiment of the present invention.
Figure 8:
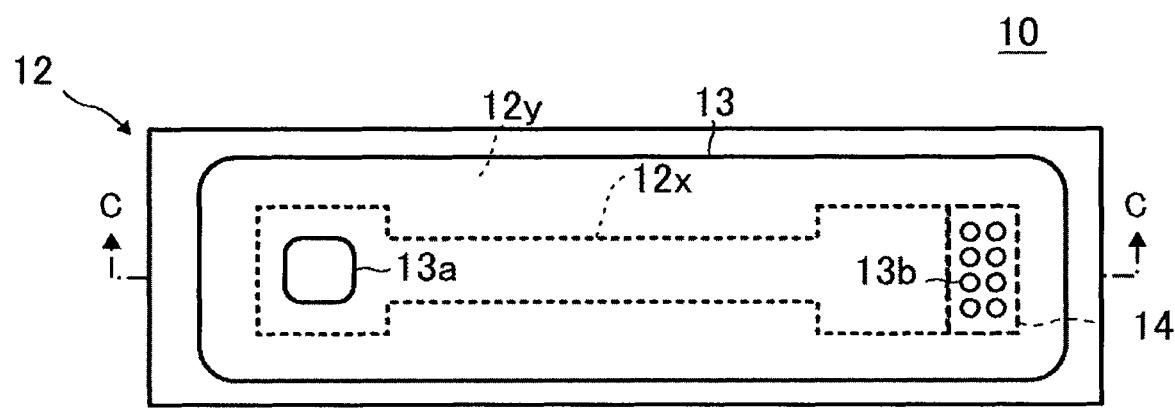
FIG. 8 is a plan view of a fluidic device according to an embodiment of the present invention.
Figure 9:
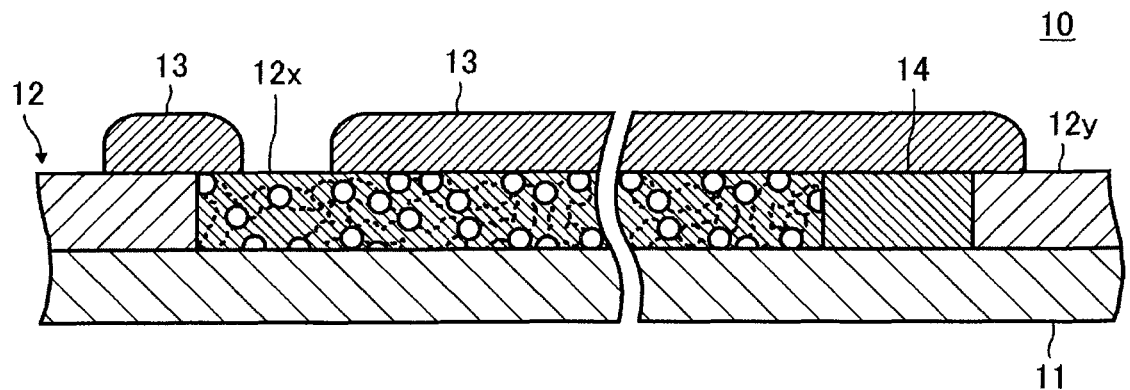
FIG. 9 is a cross-sectional diagram of a fluidic device according to an embodiment of the present invention.

The fluidic device 10 in which the absorbent member 14 is provided over the flow path member 12 has been explained (see FIG. 1 to FIG. 4). However, the present invention is not limited to the embodiment described above. It is only necessary that the absorbent member 14 contacts the porous portion 12x of the flow path member 12, and it may be formed over the base member 11. FIG. 7 is a perspective diagram of a fluidic device according to an embodiment of the present invention. FIG. 8 is a plan view of a fluidic device according to an embodiment of the present invention. FIG. 9 is a cross-sectional diagram of the fluidic device of FIG. 8 taken along a line C-C.

Conventional fluidic devices have used a fiber material as an absorbent member, and adsorbed water by a capillary action. In this case, the water absorptive capacity is proportional to the size of the capillary tubes. Therefore, as the absorption of water increases, the fiber gets swollen to narrow the capillary tubes and degrade the water absorptive capacity. Therefore, it has been necessary for the conventional fluidic devices to have a large contact area between the absorbent member and the flow path member (see JP-A Nos. 2009-63482 and 2012-189346).

On the other hand, the fluidic device of the present embodiment does not use a fiber material, but has many spherical water-absorbent polymer particles fixed on the device in a state of being conjugated by the hydrophilic polymer or being dispersed in the hydrophilic polymer. Therefore, it undergoes a smaller degradation of water absorptive capacity along with continuation of water absorption. This allows the contact area between the absorbent member 14 and the flow path member 12 to be small. Hence, it is possible to realize a compact fluidic device 10 as shown in FIG. 7 to FIG. 9.

As one embodiment of the present invention, a reagent may be placed in the pores 12a of the flow path member 12 or over the flow path member 12 in the fluidic device 10 so as for the reagent to be able to contact the liquid flowing in the flow path member 12. This allows use of the fluidic device 10 as a testing device utilizing a reaction between a reagent and a liquid. When an antibody is selected as a reagent, the fluidic device 10 can be used as an immunochromatography device as an example of a testing device. Examples of antibodies used in an immunography device include: labeled antibodies such as a gold colloid-labeled antibody (e.g., gold colloid-labeled anti-human IgG) and a labeled antibody against various allergens; antibodies such as antibodies against various allergens, e.g., anti-human IgG, a monoclonal antibody, a polyclonal antibody, a chimeric antibody, a Fab antibody, and a $(Fab)_2$ antibody; and antibodies against a labeled antibody, e.g., human IgG. Particles to label an antibody are not particularly limited to gold colloid, and other examples include any other metal colloid than gold cold, enzymatic labeling particles containing an enzyme, colorant particles containing a pigment, fluorescent particles containing a fluorescent substance, and a magnetic substance-containing particles containing a magnetic substance.

EXAMPLES

Examples of the present invention will be explained below. The present invention is not limited to these Examples by any means. In Examples and Comparative Examples described below, the voidage of the porous portion of the flow path member was calculated as described below.

<Calculation of Voidage of Porous Portion of Flow Path Member>

The voidage of the porous portion of the flow path member was calculated according to the calculation formula 1 below based on the basis weight (g/m²) and the thickness (μm) of the hydrophilic porous material, and the specific gravity of the component thereof.

$$\text{Voidage (\%)} = \{1-[\text{basis weight } (g/m^2)/\text{thickness } (\mu m)/\text{specific gravity of the component}]\} \quad [\text{Calculated Formula 1}]$$

Example 1

<Preparation of Flow Path Wall Forming Layer Coating Liquid>

An ester wax (WE-11 manufactured by NOF Corporation, with a melting start temperature of 65° C.) (100 parts by mass), montanic acid (product name: LUWAX-E manufactured by BASF Corporation, with a melting point of 76° C.) (2 parts by mass), and a long-chain alcohol represented by General Formula (1) below (where $R^1$ is an alkyl group having 28 to 38 carbon atoms, with a melting point of 75° C., manufactured by Nippon Seiro Co., Ltd.) (9 parts by mass) were dissolved at 120° C. After this, while they were stirred, morpholine (5 parts by mass) was added thereto. Then, hot water of 90° C. was dropped thereto in an amount that would result in a solid content of 30% by mass to form an oil-in-water emulsion. After this, the emulsion was cooled to thereby obtain an ester wax aqueous emulsion having a solid content of 30% by mass.

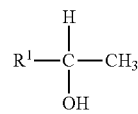

General Formula (1)

In General Formula (1), $R^1$ represents an alkyl group having 28 to 38 carbon atoms.

The average particle diameter of the obtained ester wax aqueous emulsion measured with a laser diffraction/scattering particle size distribution analyzer ("LA-920" manufactured by Horiba, Ltd.) was 0.4 µm.

Next, the obtained ester wax aqueous emulsion (with a solid content of 30% by mass) (100 parts by mass), and a carbon black water dispersion (FUJI SP BLACK 8625 manufactured by Fuji Pigment Co., Ltd., with a solid content of 30% by mass) (2 parts by mass) were mixed with each other, to thereby produce a flow path wall forming layer coating liquid.

<Preparation of Releasing Layer Coating Liquid>

A polyethylene wax (POLYWAX 1000 manufactured by Toyo ADL Corporation, with a melting point of 99° C., and a needle penetration of 2 at 25° C.) (14 parts by mass), an ethylene/vinyl acetate copolymer (EV-150 manufactured by Du Pont-Mitsui Polychemicals Co., Ltd., with a weight average molecular weight of 2,100, and VAc of 21%) (6 parts by mass), toluene (60 parts by mass), and methyl ethyl ketone (20 parts by mass) were dispersed until the average particle diameter became 2.5 µm, to thereby obtain a releasing layer coating liquid.

<Preparation of Back Layer Coating Liquid>

A silicone-based rubber emulsion (KS779H manufactured by Shin-Etsu Chemical Co., Ltd., with a solid content of 30% by mass) (16.8 parts by mass), a chloroplatinic acid catalyst (0.2 parts by mass), and toluene (83 parts by mass) were mixed, to thereby obtain a back layer coating liquid.

<Production of Transfer Member for Flow Path Member Formation>

The back layer coating liquid was applied over one side of a polyester film having an average thickness of 25 µm (LUMIRROR F65 manufactured by Toray Industries, Inc.) as a support member, and dried at 80° C. for 10 seconds, to thereby obtain a back layer having an average thickness of 0.02 µm.

Next, the releasing layer coating liquid was applied over a side of the polyester film opposite to the side over which the back layer was formed, and dried at 40° C. for 10 seconds, to thereby form a releasing layer having an average thickness of 1.5 µm.

Next, the flow path wall forming layer coating liquid was applied over the releasing layer, and dried at 70° C. for 10 seconds, to thereby form a flow path wall forming layer having an average thickness of 100 In this way, a transfer member for flow path wall formation of Example 1 was produced.

<Production of Hydrophilic Porous Base Member having Hydrophobic Substrate>

A polyester-based hot-melt adhesive (ALONMELT PES375S40 manufactured by Toagosei Co., Ltd.), as a thermoplastic resin, was heated to 190° C., and then applied over a PET film (LUMIRROR S10 manufactured by Toray Industries, Inc., with a thickness of 50 µm) to have a thickness of 50 µm with a roll coater, to thereby form an adhesive layer. The obtained applied product was kept stationary for 2 hours or longer. After this, a membrane filter made of PVDF (SVLP04700 manufactured by Merck Millipore Corporation, with a hydrophilic porous layer thickness of 125 µm, and a voidage of 70%) was overlapped with the adhesive layer-applied side, and a load of 1 kgf/cm$^2$ was applied to them at 150° C. for 10 seconds, to thereby obtain a hydrophilic porous base member having a hydrophobic substrate.

<Formation of Flow Path Wall by Thermal Transfer>

Figure 10:
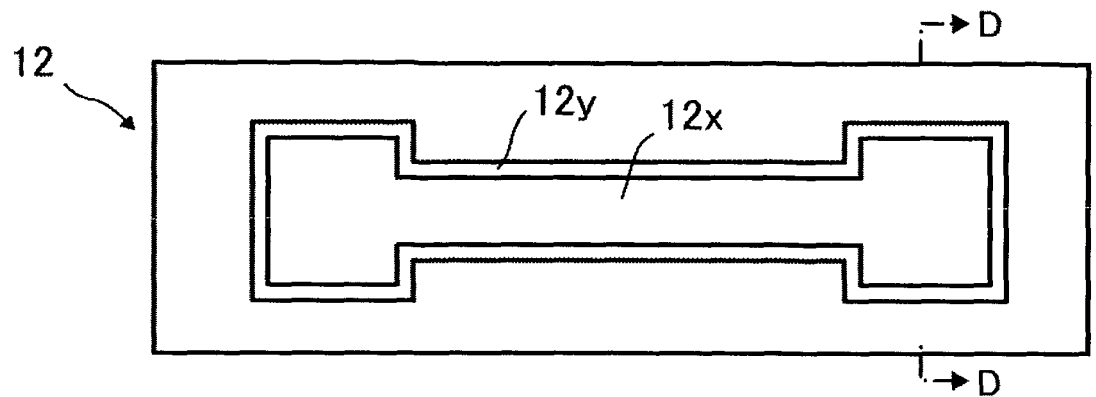
FIG. 10 is a plan view showing an example of a flow path member.
Figure 11:
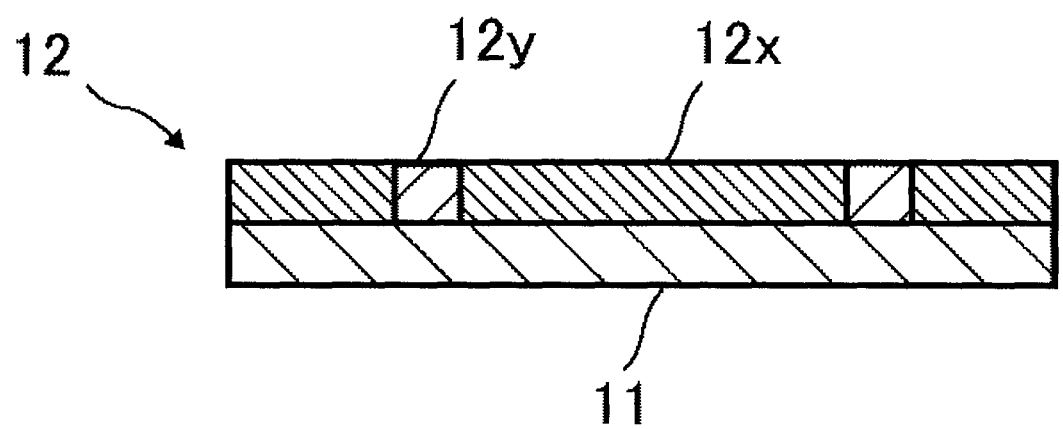
FIG. 11 is a cross-sectional diagram of the flow path member of FIG. 10 taken along a line D-D.

The transfer member for flow path wall formation was faced and overlapped with the hydrophilic porous base member having the hydrophobic substrate. After this, thermal transfer was performed with a thermal transfer printer described below under pattern formation conditions described below, to thereby form a flow path wall 12y having a pattern that was formed of a wall shown in FIG. 10 and FIG. 11. FIG. 10 is a plan view of the flow path member. FIG. 11 is a cross-sectional diagram of the flow path member of FIG. 10 taken along a line D-D. The shape of the pattern was two 10 mm×8 mm rectangles linked with a flow path having a length of 40 mm and a width of 5 mm. One of the rectangles was the portion to which to drop an analyte, and the other of the rectangles was a water-absorbing portion.

For the formation of the flow path wall, printing was performed by constructing an evaluation system with a thermal head having a head density of 300 dpi (manufactured by TDK Corporation), at a printing speed of 16.9 mm/sec, and with a printing energy of 0.81 mJ/dot.

The mass of the formed flow path member under an atmosphere having a temperature of 20° C. and a relative humidity of 65% was W1 (g).

<Preparation of Absorbent Member Formation Coating Liquid>

A highly water-absorbent resin (AQUAKEEP 10SH-NF manufactured by Sumitomo Seika Chemicals, Co., Ltd, with a volume basis average particle diameter of 25 µm) (20 parts by mass) as a water-absorbent polymer, polyvinyl pyrrolidone (POLYVINYL PYRROLIDONE 5259-100GM manufactured by Merck Millipore Corporation) (25 parts by mass) as a hydrophilic polymer, and ethanol (manufactured by Kanto Kagaku Ptd Ltd., special grade) (60 parts by mass) were dissolved and stirred at room temperature (25° C.), to thereby produce an absorbent member formation coating liquid having a resin solid content of 43% by mass.

<Production of Transfer Member for Absorbent Member Formation>

The back layer coating liquid was applied over one side of a polyester film having an average thickness of 25 µm (LUMIRROR F65 manufactured by Toray Industries, Inc.) as a support member, and dried at 80° C. for 10 seconds, to thereby form a back layer having an average thickness of 0.02 µm.

Next, the releasing layer coating liquid was applied over a side of the polyester film opposite to the side over which the back layer was formed, and dried at 40° C. for 10 seconds, to thereby form a releasing layer having an average thickness of 1.5 µm. Further, the absorbent member formation coating liquid was applied over the releasing layer, and dried at 70° C. for 300 seconds, to thereby form an absorbent member forming layer having an average thickness of 100 µm.

<Preparation of Barrier Member Forming Layer Coating Liquid>

A polyethylene wax (POLYWAX 1000 manufactured by Toyo ADL Corporation, with a melting point of 99° C., and a needle penetration of 2 at 25° C.) (14 parts by mass), an ethylene/vinyl acetate copolymer (EV-150 manufactured by Du Pont-Mitsui Polychemicals Co., Ltd., with a weight average molecular weight of 2,100, and VAc of 21%) (6 parts by mass), toluene (60 parts by mass), and methyl ethyl ketone (20 parts by mass) were dispersed until the average particle diameter became 2.5 µm, to thereby obtain an absorbent member protection layer coating liquid (releasing layer coating liquid).

<Production of Transfer Member for Barrier Member Formation>

The back layer coating liquid was applied to one side of a polyester film having an average thickness of 4.5 µm (LUMIRROR F57 manufactured by Toray Industries, Inc.) as a support member, and dried at 80° C. for 10 seconds, to thereby form a back layer having an average thickness of 0.02 μm.

<State of Voids>

First, for observation, a transfer member for absorbent member formation was cut into a test piece having a size of 20 mm×20 mm. Then, with a digital microscope (VHX-5000 manufactured by Keyence Corporation) and a zoom lens (VH-Z100R manufactured by Keyence Corporation), a surface of the transfer member on the absorbent member forming layer side was observed at a measurement magnification of ×500, to thereby observe the state of the voids.

Next, the barrier member forming layer coating liquid was applied over a side of the polyester film opposite to the side over which the back layer was formed, and dried at 40° C. for 10 seconds, to thereby form a barrier member forming layer having an average thickness of 25 μm and produce a transfer member for barrier member formation.

<Formation of Absorbent Member and Barrier Member by Thermal Transfer>

Figure 12:
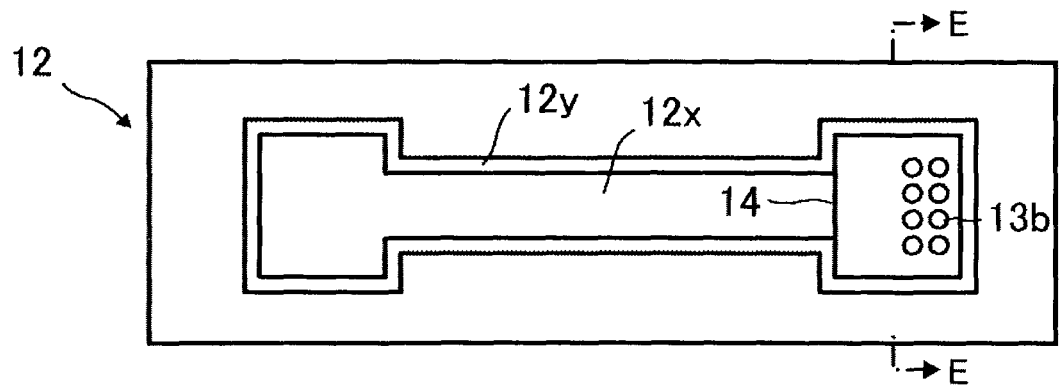
FIG. 12 is a plan view showing an example of a fluidic device.
Figure 13:
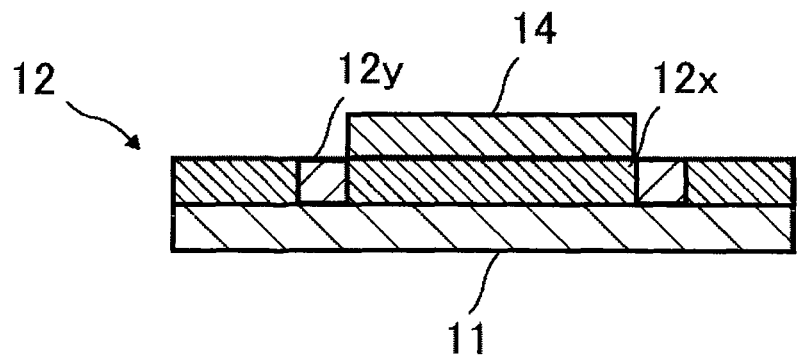
FIG. 13 is a cross-sectional diagram of the fluidic device of FIG. 12 taken along a line E-E.

Next, the transfer member for absorbent member formation and the side of the flow path member at which the flow path was provided were faced and overlapped with each other. Then, with the same thermal transfer printer as described above, thermal transfer was performed under the pattern formation conditions described below, to thereby form an absorbent member as a rectangle of 8 mm×6 mm having a thickness of 100 μm as shown in FIG. 12. FIG. 12 is a plan view of the fluidic device. FIG. 13 is a cross-sectional diagram of the fluidic device of FIG. 12 taken along a line E-E.

For the formation of the absorbent member, printing was performed by constructing an evaluation system with a thermal head having a head density of 300 dpi (manufactured by TDK Corporation), at a printing speed of 16.9 mm/sec, and with a printing energy of 0.28 mJ/dot. The mass of the fabricated fluidic device under an atmosphere having a temperature of 20° C. and a relative humidity of 65% was W2 (g).

Further, the transfer member for barrier member formation and the side of the flow path member at which the flow path was provided were faced and overlapped with each other. After this, with the same thermal transfer printer as described above and under the pattern formation condition described below, a barrier member was formed as a rectangle of 10 mm×8 mm covering at least a portion of the absorbent member.

For the formation of the barrier member, printing was performed by constructing an evaluation system with a thermal head having a head density of 300 dpi (manufactured by TDK Corporation), at a printing speed of 16.9 mm/sec, and with a printing energy of 0.28 mJ/dot. The mass of the fabricated fluidic device under an atmosphere having a temperature of 20° C. and a relative humidity of 65% was W3 (g).

<Evaluation of Water Absorptivity>

The fluidic device was put horizontally, water was dropped into the sample dropping region, and dropping was continued for so long as water absorption by the absorbent member could be observed. The mass of the water-absorbed fluidic device after 10 minutes passed since the dropping was completed was measured as a mass W4 (g). Then, the water absorptivity of the absorbent member was calculated according to the following formula. The result is shown in Table 1.

Water absorptivity=[W4−{W3−(W2−W1)}]/(W2−W1)×100

Further, water absorptive capacity was evaluated based on the criteria below. The results are shown in Table 1 together with the results of other evaluations described later.

[Evaluation Criteria]

A: 30,000% or greater

This is a range in which an analyte liquid can be sufficiently absorbed without flowing back, even though the absorbent member is in a small amount with respect to the size of the testing kit.

B: 10,000% or greater but less than 30,000%

This is a range in which an analyte liquid can be sufficiently absorbed without flowing back, when the absorbent member is in a suitable amount with respect to the size of the testing kit.

C: 2,000% or greater but less than 10,000%

This is a range in which an analyte liquid flows back, and the water absorptive capacity is slightly short.

D: 0% or greater but less than 2,000%

This is a range in which the water absorptive capacity is extremely short, and the absorbent member cannot be used in the testing kit.

Example 2

The fluidic device of Example 2 was fabricated in the same manner as in Example 1, except that in the production of an absorbent member formation coating liquid, SUNWET (1M1000MPS manufactured by Sanyo Kasei Co., Ltd, with a particle diameter of from 25 μm to 50 μm) was used instead of AQUAKEEP. The same evaluation as in Example 1 was also performed. The result is shown in Table 1.

Example 3

In the production of an absorbent member formation coating liquid, SUMIKAGEL S-50 (manufactured by Sumitomo Chemical Company, Limited) was used instead of AQUAKEEP, and particles thereof were classified with a sieve having a 200 mesh, to thereby obtain a water-absorbent polymer having a volume basis average particle diameter of 28 μm. The fluidic device of Example 3 was fabricated in the same manner as in Example 1, except that the classified water-absorbent polymer particles were used. The same evaluation as in Example 1 was also performed. The result is shown in Table 1.

Example 4

The fluidic device of Example 4 was fabricated in the same manner as in Example 1, except that in the production of an absorbent member formation coating liquid, polyethylene oxide (ALKOX L-6 manufactured by Meisei Chemical Works, Ltd.) was used instead of polyvinyl pyrrolidone. The same evaluation as in Example 1 was also performed. The result is shown in Table 1.

Example 5

The fluidic device of Example 5 was fabricated in the same manner as in Example 1, except that in the production of an absorbent member formation coating liquid, a polybutyral resin (ESLEC BL-1 manufactured by Sekisui Chemical Co., Ltd.) was used instead of polyvinyl pyrrolidone. The same evaluation as in Example 1 was also performed. The result is shown in Table 1.

Comparative Example 1

A highly water-absorbent resin "AQUALIC CA (W4S)" manufactured by Nippon Shokubai Co., Ltd. (with an average particle diameter of from 100 μm to 300 μm) was used as highly water-absorbent polymer particles. A hygienic base paper (tissue paper base paper) "NPE" manufactured by Okura Paper Manufacturing Co., Ltd. was used as a water-absorbent surface sheet.

An adhesive made of a polyamide/epichlorohydrin resin was sprayed over one side of the surface sheet (8.5 g/m$^2$), and pulp (180 g/m$^2$) and the highly water-absorbent polymer particles (56 g/m$^2$) were diffused uniformly over the one side. After this, such surface sheets (8.5 g/m$^2$) were layered. The obtained layered material (surface sheet/pulp and highly water-absorbent polymer particles/surface sheet) was heated and applied with pressure-bonding at some portions according to an embossing technique, to thereby produce an absorbent pad. The thickness of the absorbent pad was 0.8 mm, and recessed portions appeared on the surface of the absorbent pad by the heating and pressure-bonding had a diameter of 1.0 mm, and the abundance density of such recessed portions was 30 recesses/cm$^2$. The mixing ratio between the pulp component (a total of tissue paper and pulp) and the highly water-absorbent polymer particles in the absorbent pad was 78% by mass=22% by mass. The obtained absorbent pad was pasted over the absorbing portion of the flow path member that was formed in Example 1 by thermal transfer.

The mass of the flow path member under an atmosphere having a temperature of 20° C. and a relative humidity of 65% before the absorbent pad was pasted over the absorbing portion was W1 (g), and the mass of the flow path member under the same atmosphere after it was pasted was W2 (g).

Further, the absorbent pad was entirely covered with FILMOLUX 609 manufactured by Filmolux Co., Ltd. which had a shape of a rectangle of 10 mm×8 mm.

The mass of the fabricated fluidic device under an atmosphere having a temperature of 20° C. and a relative humidity of 65% was W3 (g).

The same evaluation as in Example 1 was also performed. The mass of the water-absorbed fluidic device when 10 minutes passed was W4 (g). The result is shown in Table 1.

Comparative Example 2

An acrylic acid aqueous solution (50 g of acrylic acid in 374.91 g of water) that contains dimethylamino ethyl acrylate in an amount of about 3 mol % relative to acrylic acid was neutralized with a sodium hydroxide (NaOH) solution under cooling conditions. The degree of neutralization was about 50 mol %, and the total monomer concentration was 10% by mass. The monomer solution (500 g) was cooled to 10° C., and purged with nitrogen for 5 minutes. Then, 1% by mass $H_2O_2$ (10 g), 2.01% by mass sodium persulfate (19.90 g), 2.27% by mass azobis-2-amidinopropane dihydrochloric acid (4.41 g), and 0.5% by mass sodium erythorbate (10 g) were added thereto. Provided that polymerization would not start in 5 minutes, a few drops of a $FeSO_4$ aqueous solution would be added thereto to start the reaction. The monomer solution became a very viscous solution in about 2 hours. The obtained viscous polymer solution was cooled to room temperature so as to be prepared for use.

The water-soluble pre-highly water-absorbent polymer prepared as above was diluted with water such that the solid content thereof would be from 1% by mass to 2% by mass. In order to produce 1 kg of paste, the obtained solution of the diluted polymer (950 g to 970 g) was sufficiently mixed at room temperature with a commercially available highly water-absorbent polymer FAVOR SXM880 (manufactured by Evonik Stockhausen GmbH) (about 30 g to 50 g).

Instead of transferring an absorbent member as in Example 1, the water-absorbent polymer obtained as above was applied over a water absorbing portion, and dried at 100° C. for 30 minutes. The mass of the fluidic device (flow path member) under an atmosphere having a temperature of 20° C. and a relative humidity of 65% before the polymer was applied over the absorbing portion was W1 (g), and the mass of the fluidic device (flow path member) under the same atmosphere after it was applied was W2 (g). Further, the mass of the water-absorbed fluidic device when 10 minutes passed in the same evaluation as in Example 1 was W4 (g). All of the other steps than the steps described above were the same as in Example 1 in fabricating and evaluating the fluidic device. However, in the present case, the water-absorbent polymer soaked into the flow path member, and the polymer particles having reached water absorption saturation banked up within the flow path, which made it impossible to obtain a sufficient water absorptivity. The result is shown in Table 2 Table 1.

Example 2-1

<Production of Transfer Member for Flow Path Wall Formation>

A transfer member for flow path wall formation was produced with the same materials and in the same manner as in Example 1.

<Production of Hydrophilic Porous Base Member having Hydrophobic Substrate>

A hydrophilic porous base member having a hydrophobic substrate was obtained with the same materials and in the same manner as in Example 1.

<Formation of Flow Path Wall by Thermal Transfer>

A flow path wall was formed in the hydrophilic porous base member having a hydrophobic substrate with the same materials and in the same manner as in Example 1, to thereby form a flow path member. The mass of the formed flow path member under an atmosphere having a temperature of 20° C. and a relative humidity of 65% was W1 (g).

<Preparation of Absorbent Member Formation Coating Liquid>

A highly water-absorbent resin (AQUAKEEP 10SH-NF manufactured by Sumitomo Seika Chemicals, Co., Ltd., with a volume basis average particle diameter of 25 μm) (16 parts by mass) as a water-absorbent polymer, polyvinyl butyral (ESLEC BX-1 manufactured by Sekisui Chemical Co., Ltd.) (0.8 parts by mass) as a hydrophilic polymer, and ethanol (manufactured by Kanto Kagaku Ptd Ltd., special grade) (100 parts by mass) were dissolved and stirred at room temperature (25° C.), to thereby produce an absorbent member formation coating liquid having a resin solid content of 14% by mass.

<Production of Transfer Member for Absorbent Member Formation>

The back layer coating liquid prepared in Example 1 was applied over one side of a polyester film having an average thickness of 25 μm (LUMIRROR F65 manufactured by Toray Industries, Inc.) as a support member, and dried at 80°

C. for 10 seconds, to thereby form a back layer having an average thickness of 0.02 µm.

Next, the releasing layer coating liquid prepared in Example 1 was applied over a side of the polyester film opposite to the site over which the back layer was formed, and dried at 40° C. for 10 seconds, to thereby form a releasing layer having an average thickness of 1.5 µm. Further, the absorbent member formation coating liquid was applied over the releasing layer, and dried at 70° C. for 120 seconds, to thereby form an absorbent member forming layer having an average thickness of 100 µm.

<Preparation of Barrier Member Forming Layer Coating Liquid>

An absorbent member protection layer coating liquid (releasing layer coating liquid) was obtained with the same materials and in the same manner as in Example 1.

<Production of Transfer Member for Barrier Member Formation>

A transfer member for barrier member formation was produced with the same materials and in the same manner as in Example 1.

<Formation of Absorbent Member and Barrier Member by Thermal Transfer>

An absorbent member was formed over the flow path member with the same materials and in the same manner as in Example 1. The mass of the fluidic device in which the absorbent member was formed under an atmosphere having a temperature of 20° C. and a relative humidity of 65% was W2 (g).

Further, a barrier member was formed over the flow path member with the same materials and in the same manner as in Example 1. The mass of the fluidic device in which the barrier member was formed under an atmosphere having a temperature of 20° C. and a relative humidity of 65% was W3 (g).

<Evaluation of Water Absorptivity>

Evaluation was performed in the same manner as in Example 1. The result is shown in Table 1.

Example 2-2

A fluidic device of Example 2-2 was fabricated in the same manner as in Example 2-2, except that in the production of an absorbent member formation coating liquid, SUNWET (1M1000MPS manufactured by Sanyo Kasei Co., Ltd, with a particle diameter of from 25 µm to 50 µm) was used instead of AQUAKEEP. Further, the same evaluation as in Example 1 was performed. The result is shown in Table 1.

Example 2-3

In the production of an absorbent member formation coating liquid, SUMIKAGEL S-50 (manufactured by Sumitomo Chemical Company, Limited, with a volume basis average particle diameter of 200 µm) was used instead of AQUAKEEP, and particles of SUMIKAGEL were classified through a sieve having a 200 mesh, to thereby obtain a water-absorbent polymer having a volume basis average particle diameter of 28 µm. A fluidic device of Example 2-3 was fabricated in the same manner as in example 2-1, except that the obtained classified water-absorbent polymer particles were used. Further, the same evaluation as in Example 1 was performed. The result is shown in Table 1.

Example 2-4

<Production of Paper Base Member>

Figure 17A:
FIG. 17A is a plan view showing an example of a fluidic device according to an Example.
Figure 17B:
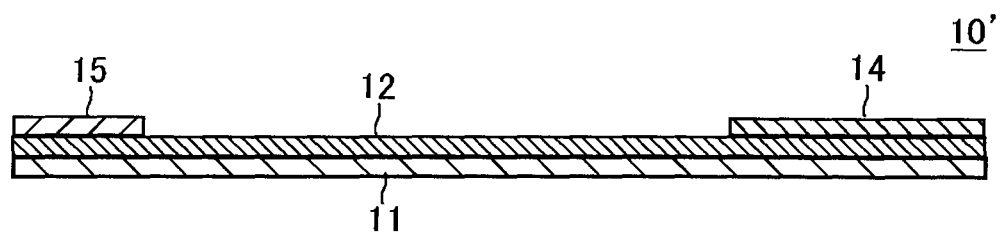
FIG. 17B is a cross-sectional diagram of FIG. 17A taken along a line F-F.

FIG. 17A is a plan view of a fluidic device 10' according to Example 2-4. FIG. 17B is a cross-sectional diagram of the fluidic device 10' shown in FIG. 17A taken along a line F-F. A hydrophilic porous base member having a hydrophobic substrate was produced in the same manner as in Example 1, cut into a size of 5 mm on width×64 mm on length, to thereby obtain a paper base member (a base member 11 and a flow path member 12).

<Formation of Sample Dropping Region>

As shown in each of FIG. 17A and FIG. 17B, a sample pad 15 having a size of 5 mm on width×8 mm on length (CFSP223000 manufactured by Merck Millipore Corporation) was placed and pasted over a region that ranged from a longer-axis-direction one end of the paper base member to a position that was 8 mm away therefrom, to thereby form a sample dropping region. The mass of the sample pad-pasted paper base member under an atmosphere having a temperature of 20° C. and a relative humidity of 65% was W1 (g).

<Formation of Absorbent Member by Thermal Transfer>

Next, as shown in each of FIG. 17A and FIG. 17B, an absorbent member 14 was formed over a region that ranged from a longer-axis-direction one end of the paper base member opposite to the sample dropping region to a position that was 16 mm away therefrom, with the same transfer member for absorbent member formation and under the same experimental conditions as in Example 2-1. The mass of the resultant under an atmosphere having a temperature of 20° C. and a relative humidity of 65% was W2 (g).

<Formation of Barrier Member by Thermal Transfer>

Next, a barrier member was formed over the formed absorbent member 14 with the same transfer member for barrier member formation and under the same experimental conditions as in Example 2-1, to thereby obtain a paper base member (fluidic device 10') having an absorbing area. The mass of the paper base member over which the absorbing area was formed under an atmosphere having a temperature of 20° C. and a relative humidity of 65% was W3 (g). A side of the paper base member having the absorbing area at which the sample pad was placed was the analyte dropping position, and the opposite side thereof was the water absorbing portion.

<Evaluation of Water Absorptivity>

Evaluation of water absorptivity of the paper base member over which the absorbing area was formed was performed in the same manner as in Example 1. The result is shown in Table 1.

TABLE 1

| | Absorbent member | | | | |
| --- | --- | --- | --- | --- | --- |
| No. | Water-absorbent polymer | Hydrophilic polymer | State of voids | Barrier member | Absorptivity (%) |
| Ex. 1 | AQUAKEEP | PVP | Almost absent | Polyethylene wax | B 13,800 |

TABLE 1-continued

| No. | Constituent materials | State of voids | Barrier member | Absorptivity (%) |
|---|---|---|---|---|
| Ex. 2 | SUNWET | PVP | Almost absent | Polyethylene wax | B 14,200 |
| Ex. 3 | SUMIKAGEL | PVP | Almost absent | Polyethylene wax | B 14,000 |
| Ex. 4 | AQUAKEEP | ALKOX | Almost absent | Polyethylene wax | B 14,400 |
| Ex. 5 | AQUAKEEP | ESLEC B | Almost absent | Polyethylene wax | B 12,000 |
| Ex. 2-1 | AQUAKEEP | ESLEC B | Present | Polyethylene wax | A 38,400 |
| Ex. 2-2 | SUNWET | ESLEC B | Present | Polyethylene wax | A 38,800 |
| Ex. 2-3 | SUMIKAGEL | ESLEC B | Present | Polyethylene wax | A 37,800 |
| Ex. 2-4 | AQUAKEEP | ESLEC B | Present | Polyethylene wax | A 38,300 |
| Comp. Ex. 1 | Materials described in Comp. Ex. 1 | Present | FILMOLUX | C 5,000 |
| Comp. Ex. 2 | Materials described in Comp. Ex. 2 | Almost absent | Polyethylene | C 3,000 |

Example 6

<Production of Hydrophilic Porous Base Member having Hydrophobic Substrate>

A polyester-based hot-melt adhesive (ALONMELT PES375S40 manufactured by Toagosei Co., Ltd.), as a thermoplastic resin, was heated to 190° C., and then applied over a PET film (LUMIRROR S10 manufactured by Toray Industries, Inc. with a thickness of 50 μm) to have a thickness of 50 μm with a roll coater, to thereby form an adhesive layer. The obtained applied product was kept stationary for 2 hours or longer. After this, a nitrocellulose membrane filter (HIFLOW PLUS HF075UBXSS manufactured by Merck Millipore Corporation, with a thickness of 135 μm, and a voidage of 70%) was overlapped with the adhesive layer-applied side, and a load of 1 kgf/cm² was applied to them at 150° C. for 10 seconds, to thereby obtain a hydrophilic porous base member having a hydrophobic substrate. A blocking treatment described below was applied to the substrate.

[Blocking Treatment]

The nitrocellulose membrane filter was immersed in a blocking agent (a BSA-containing PBS solution (with pH of 7.4), P3688-10PAK manufactured by Sigma-Aldrich Co., LLC.), and shaken gently for 20 minutes. After this, any excess moisture on the surface of the filter was sucked away, and the filter was dried at room temperature for 1 hour.

<Fabrication of Fluidic Device>

Figure 14:
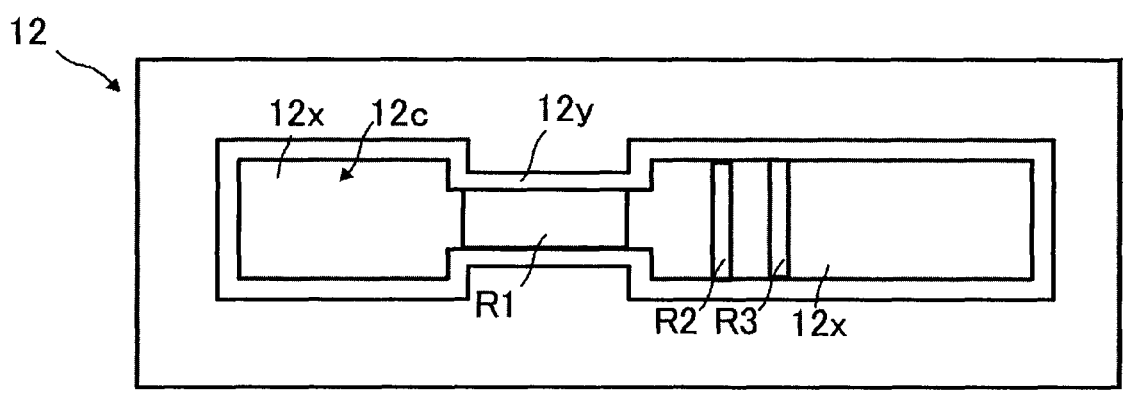
FIG. 14 is a plan view showing an example of a flow path member.

The same transfer member as the transfer member for flow path wall formation produced in Example 1 was faced and overlapped with the above hydrophilic porous base member having the hydrophobic substrate. Then, under the same experimental conditions as in Example 1, thermal transfer was performed under pattern formation conditions described below, to thereby form a flow path wall 12y having a pattern that was formed of a wall having a width of 700 μm shown in FIG. 14. FIG. 14 is a plan view of the flow path member.

Figure 15:
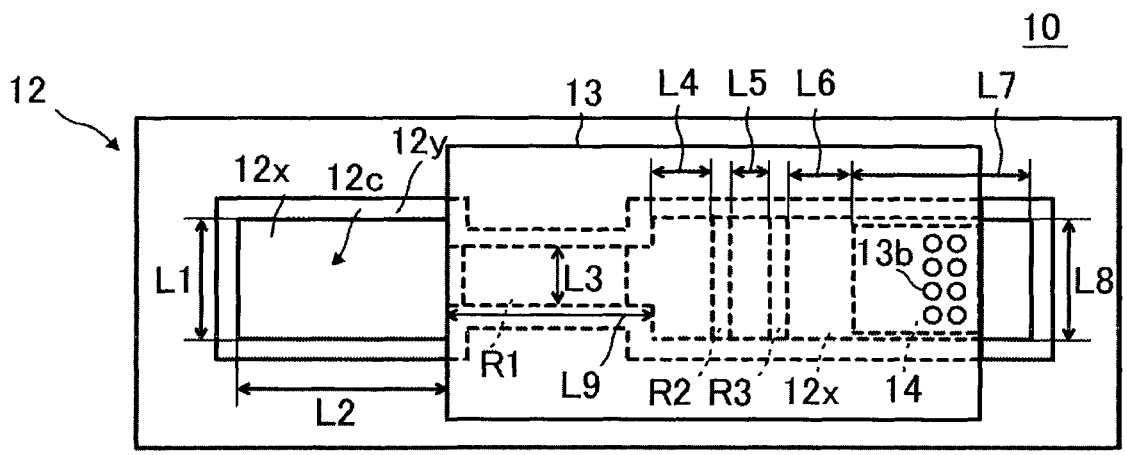
FIG. 15 is a plan view showing an example of a fluidic device.

Next, an absorbent member 14 shown in FIG. 15 was formed with the same transfer member for absorbent member and barrier member formation as in Example 1 and under the same experimental conditions as in Example 1, to thereby obtain a fluidic device that included a flow path, reaction fields, and an absorbing area. FIG. 15 is a plan view of the fluidic device. The lengths L1 to L9 in FIG. 15 are as follows.

L1: 5 mm
L2: 17 mm
L3: 3 mm
L4: 5 mm
L5: 5 mm
L6: 5 mm
L7: 17 mm
L8: 5 mm
L9: 17 mm

Next, as a test line, an anti-human IgG antibody (4.7 mg/mL, 11886 manufactured by Sigma-Aldrich Co., LLC) (6 μL) was applied over a formed reaction field R2 to have a width of 1 mm. As a control line, a human IgG (4.8 mg/mL, 12511-10MG manufactured by Sigma-Aldrich Co., LLC) (6 μL) was applied over a reaction field R3 to have a width of 1 mm. Then, they were dried at room temperature for 30 minutes to 60 minutes.

Next, as a gold colloid-labeled antibody, a gold colloid-labeled anti-human IgG (Gold 40 nm, OD=15, manufactured by Bioassay Works, LLC) (5 μL) was applied over a reaction field R1. Further, a barrier member was formed in the same manner as in Example 1 so as to completely cover the absorbent member as shown by the barrier member 13 in FIG. 15, to thereby obtain a fluidic device for immunochromatography (I).

Figure 16:
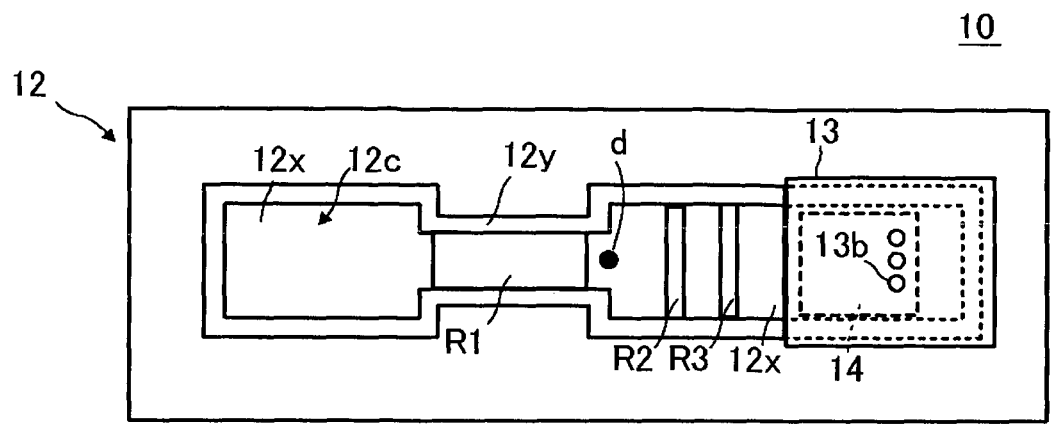
FIG. 16 is a plan view showing an example of a fluidic device.

After the gold colloid-labeled antibody was applied, a dot having a diameter of 1 mm was formed with a permanent marker (MEF-12EU-R manufactured by Pilot Corporation) at a position shown in FIG. 16 for evaluation of a speed. Further, a barrier member was formed in the same manner as in Example 1 so as to completely cover the absorbent member, as shown by a barrier member 13 in FIG. 16, to thereby obtain a fluidic device for immunochromatography (II). FIG. 16 is a plan view of the fluidic device.

<Judgment of Smudging of Detection Regions>

Human IgG diluted with purified water to a 2 mg/ml solution was dropped in an amount of 50 μL into the sample area (i.e., a dropping region 12c) of the fluidic device for immunochromatography (I) fabricated as above, and emergence of lines having a width of 1 mm was waited in the reaction field R2 (test line) and the reaction field R3 (control line). After the emergence of such lines was confirmed, smudging of the lines was observed after 15 minutes passed. The smudged conditions of the lines were evaluated based on the evaluation criteria below. The result is shown in Table 2.

[Evaluation Criteria]

A: No smudging was observed, and the lines were clear.

B: Slight smudging of the lines was observed.

C: Smudging of the lines was observed, but judgment was narrowly possible.

D: Smudging was serious, and judgment was impossible.

<Evaluation of Water Absorption Speed>

Human IgG diluted with purified water to a 2 mg/ml solution was dropped in an amount of 50 μL into the sample area (i.e., a dropping region 12c) of the fluidic device for immunochromatography (II) fabricated as above, and it was observed how the dot was chromatographed by having the analyte liquid flowing, and how the dot moved by drawing a locus in the direction in which the analyte liquid flowed. With respect to the timing at which the analyte liquid reached the absorbent member and started to be absorbed, which was regarded as a start (0 second), the time T (second) taken until the length of the locus of the dot became 5 mm was measured as an indicator of the water absorption speed.

The time T was evaluated based on the evaluation criteria below. The result is shown in Table 2.

[Evaluation Criteria]

A: 140 seconds or longer but shorter than 200 seconds

This is a range in which when the time is converted to, for example, a time T' taken for the analyte liquid to flow by 40 mm, it corresponds to a range of 125 seconds or longer but shorter than 175 seconds, and for a practical purpose, testing can be performed with a good sensitivity in a short time.

B: 200 seconds or longer but shorter than 260 seconds

This is a range in which when the time is converted to, for example, a time T' taken for the analyte liquid to flow by 40 mm, it corresponds to a range of 175 seconds or longer but shorter than 225 seconds, and testing can be performed with a good sensitivity in a practical time.

C: 260 seconds or longer but shorter than 320 seconds

This is a range in which when the time is converted to, for example, a time T' taken for the analyte liquid to flow by 40 mm, it corresponds to a range of 225 seconds or longer but shorter than 275 seconds, and for a practical purpose, a long time is taken for the testing, and the water absorption speed is low, although the sensitivity is good. D: 320 seconds or longer The water absorption speed is low, and beyond the practically usable range.

Example 3-1

A fluidic device of Example 3-1 was fabricated in the same manner as in Example 6, except that unlike in Example 6, the materials and the manner of Example 5 were used in the formation of the absorbent member. Evaluation of smudging of the detection region and evaluation of the water absorption speed were performed in the same manner as in Example 6. The results are shown in Table 2.

Example 3-2

A fluidic device of Example 3-2 was fabricated in the same manner as in Example 6, except that unlike in Example 6, the materials and the manner of Example 2-1 were used in the formation of the absorbent member. Evaluation of smudging of the detection region and evaluation of the water absorption speed were performed in the same manner as in Example 6. The results are shown in Table 2.

Example 3-3

<Production of Paper Base Member>

A hydrophilic porous base member having a hydrophobic substrate was produced and subjected to a blocking treatment in the same manner as in Example 6, to thereby obtain a paper base member (flow path member 12).

<Formation of Absorbent Member and Barrier Member by Thermal Transfer>

Figure 18A:
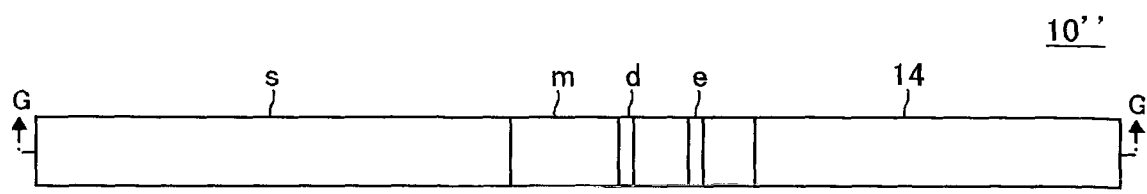
FIG. 18A is a plan view showing an example of a fluidic device according to an Example.
Figure 18B:
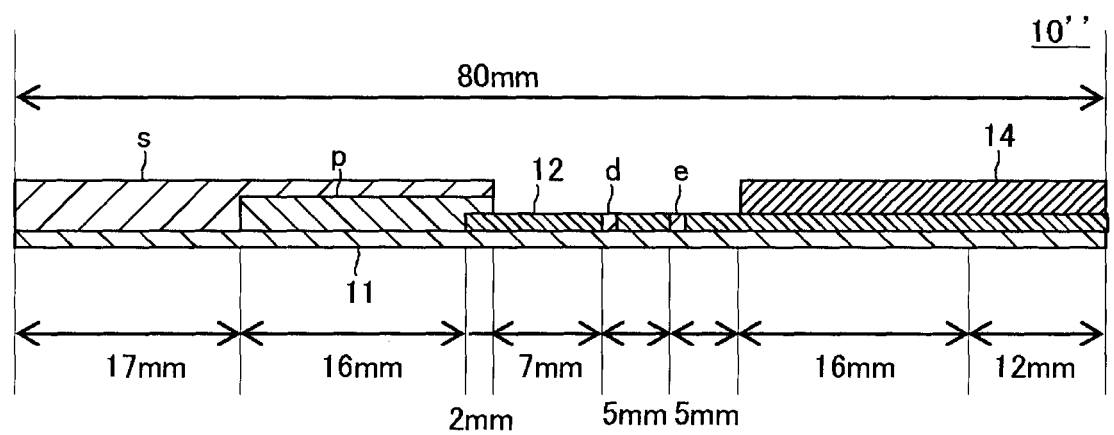
FIG. 18B is a cross-sectional diagram of FIG. 18A taken along a line G-G.

FIG. 18A is a plan view of a fluidic device 10" according to Example 3-3. FIG. 18B is a cross-sectional diagram of the fluidic device 10" of FIG. 18A taken along a line G-G. FIG. 18B shows values representing sizes. However, the present invention is not limited to the sizes shown, and a person who practices the present invention may change the values arbitrarily.

With the same transfer member for absorbent member and barrier member formation and under the same experimental conditions as in Example 2-1, an absorbent member 14 was formed over a region that ranged from a longer-axis-direction one end of the paper base member cut into a size of 4 mm on width×47 mm on length to a position that was 28 mm away therefrom as shown in each of FIG. 18A and FIG. 18B, to thereby obtain a paper base member having an absorbing area.

<Formation of Test Line and Control Line as Stationary Phase>

An anti-human IgG antibody (11886, 4.7 mg/mL, manufactured by Sigma-Aldrich Co., LLC) (6 μL) was applied as a test line over the paper base member having an absorbing area at a d position that was 9 mm away from a shorter-axis-direction one end thereof to have a width of 1 mm, as shown in FIG. 18A and FIG. 18B. Then, human IgG (12511-10MG, 4.8 mg/mL, manufactured by Sigma-Aldrich Co., LLC) (6 μL) was applied as a control line at an e position that was 5 mm away from the d position to have a width of 1 mm. After this, the lines were dried at room temperature for 30 minutes to 60 minutes.

<Production of Labeled-Antibody Retaining Pad>

A gold colloid-labeled anti-human IgG antibody was adjusted to OD=2 with a labeled antibody diluting fluid. The labeled antibody reagent coating liquid was applied over a glass fiber pad (GFCP203000 manufactured by Merck Millipore Corporation, shown by p in FIG. 18B) cut into a size of 4 mm on width×18 mm on length to be 60 μL/cm², and dried at reduced pressure over night, to thereby produce a labeled antibody retaining pad.

<Assembly of Testing Device>

The paper base member having an absorbing area was bonded to a PET film (LUMIRROR S10 manufactured by Toray Industries, Inc., 100 μm) cut into a size of 4 mm on width×80 mm on length at a position that was 33 mm away from a longer-axis-direction one end of the PET film (base member 11), such that a side of the paper base member opposite to the side thereof over which the reagent was applied was faced with the PET film.

Next, the labeled antibody dried pad produced as above that was cut into a size of 4 mm on width×18 mm on length was placed and pasted over the upper side of the paper base member so as to overlap with the upstream end of the paper base member by 2 mm. Further, a sample pad having a size of 4 mm on width×35 mm on length (CFSP223000 manufactured by Merck Millipore Corporation, shown by s in FIG. 18A and FIG. B) was placed and pasted over the upper side of the labeled antibody retaining pad so as to overlap therewith by 18 mm, to thereby form a sample dropping pad. In this way, a testing device (fluidic device 10") was fabricated. Evaluation of smudging of the detection region and evaluation of the water absorption speed were performed for the fabricated testing device in the same manner as in Example 6. The results are shown in Table 2.

Comparative Example 3

A fluidic device of Comparative Example 3 was fabricated in the same manner as in Example 6, except that instead of forming the absorbent member of Example 6, the water-absorbent pad produced in Comparative Example 1 was pasted and covered with a film (FILMOLUX 609 manufactured by Filmolux Co., Ltd.). Evaluation of smudging of the detection region and evaluation of the water absorption speed were performed in the same manner as in Example 6. The results are shown in Table 2.

Comparative Example 4

A fluidic device of Comparative Example 4 was fabricated in the same manner as in Example 6, except that instead of forming the absorbent member of Example 6, the water-absorbent polymer produced in Comparative Example 2 was applied and dried. Evaluation of smudging of the detection region and evaluation of the water absorption speed were performed in the same manner as in Example 6. The results are shown in Table 2.

of the water up to the control line and the test line. In Comparative Example 4, water-absorbent polymer particles that had soaked into the flow path member banked up the flow of the analyte liquid in the flow path, to thereby make it impossible to obtain a sufficient water absorptivity. It was considered that as a result, the analyte liquid stagnated in the vicinity of the lines and made the lines unclear.

Aspects of the present invention are as follows, for example.

<1> A fluidic device, including:
a porous flow path member;
an absorbent member contacting the flow path member, and configured to absorb a liquid; and
a barrier member covering at least a portion of the absorbent member,
wherein the absorbent member contains a liquid-absorbent polymer that absorbs the liquid, and a lyophilic polymer having lyophilicity to the liquid.

<2> The fluidic device according to <1>,
wherein the liquid-absorbent polymer is conjugated by the lyophilic polymer, and voids are formed in the absorbent member.

<3> The fluidic device according to <1> or <2>,
wherein the absorbent member has a continuous cell.

<4> The fluidic device according to any one of <1> to <3>,
wherein the liquid-absorbent polymer is a water-absorbent polymer, and
wherein the lyophilic polymer is a water-insoluble hydrophilic polymer.

<5> The fluidic device according to <1>,
wherein the liquid-absorbent polymer is dispersed in the lyophilic polymer in the absorbent member.

TABLE 2

| No. | Absorbent member | | | | Water | | |
| --- | --- | --- | --- | --- | --- | --- | --- |
| | Water-absorbent polymer | Hydrophilic polymer | State of voids | Barrier member | Smudging | absorption speed | Water absorptivity |
| Ex. 6 | AQUAKEEP | PVP | Almost absent | Polyethylene wax | A | B | B |
| Ex. 3-1 | AQUAKEEP | ESLEC B | Present | Polyethylene wax | A | B | A |
| Ex. 3-2 | AQUAKEEP | ESLEC B | Almost absent | Polyethylene wax | A | C | B |
| Ex. 3-3 | AQUAKEEP | ESLEC B | Present | Polyethylene wax | A | B | A |

| No. | Absorbent member | | | Water | | |
| --- | --- | --- | --- | --- | --- | --- |
| | Constituent materials | State of voids | Barrier member | Smudging | absorption speed | Water absorptivity |
| Comp. Ex. 3 | Materials described in Comp. Ex. 3 | Present | Polyethylene wax | C | A | C |
| Comp. Ex. 4 | Materials described in Comp. Ex. 4 | Almost absent | Polyethylene wax | C | D | C |

Note that a fiber absorbent member was provided in the fluidic device of Comparative Example 3. This fiber absorbent member had an advantage of being able to absorb water in a short time, but was poor in the performance for retaining water once absorbed, hence allowed the water absorbed in the absorbent member to flow back into the flow path member as the flow path dried up. It was considered that the lines were smudged and became unclear because the lines that had developed a color were re-eluted upon flowing back <6> The fluidic device according to <5>,
wherein the liquid-absorbent polymer is a water-absorbent polymer, and
wherein the lyophilic polymer is a water-soluble hydrophilic polymer.

<7> The fluidic device according to any one of <1> to <6>,
wherein the liquid-absorbent polymer is particles having a volume basis average particle diameter of 60 μm or less.

<8> The fluidic device according to any one of <1> to <7>, wherein the barrier member has a gas barrier property.
<9> The fluidic device according to any one of <1> to <8>, wherein the fluidic device is an immunochromatography device.
<10> A transfer member for fluidic device fabrication, including:
a support member;
a releasing layer stacked over the support member; and
an absorbent member forming layer stacked over the releasing layer, and containing a liquid-absorbent polymer that absorbs a liquid, and a lyophilic polymer having lyophilicity to the liquid,
wherein the absorbent member forming layer contains a thermoplastic material.
<11> A method for fabricating a fluidic device, including:
bringing the absorbent member forming layer of the transfer member according to <10> and a porous flow path member into contact with each other, and applying heat and pressure to the transfer member to thereby transfer the absorbent member forming layer onto the flow path member.

REFERENCE SIGNS LIST 10 fluidic device
11 base member
12 flow path member
12a, 12b pore
12c dropping region
12x porous portion
12y flow path wall
13 barrier member
14 absorbent member
100 transfer member for flow path wall formation
101 support member
102 releasing layer
103 back layer
112y flow path wall forming layer
200 transfer member
201 support member
202 releasing layer
203 back layer
214 absorbent member forming layer

The invention claimed is:

1. A fluidic device, comprising:
a porous flow path member;
an absorbent member in contact with the flow path member and configured to absorb a liquid, wherein the absorbent member does not comprise a fiber material; and
a barrier member disposed over and covering at least a portion of the absorbent member and being in contact with a flow path wall of the porous flow path member,
wherein the barrier member is a film or a laminate that has a water gas permeability of 100 g/(m$^2$·day) or less, and wherein a thickness of the barrier member is from 5 µm to 100 µm,
wherein the absorbent member comprises a liquid-absorbent polymer that absorbs the liquid, and a lyophilic polymer having lyophilicity to the liquid, wherein liquid-absorbent polymer is conjugated by the lyophilic polymer in the absorbent member such that voids are formed in the absorbent member, wherein a voidage in the absorbent member is from 30% to 85%, and wherein a ratio of the lyophilic polymer in the absorbent member is from 1% to 60% by mass, and
wherein the fluidic device does not comprise a housing.

2. The fluidic device according to claim 1, wherein the absorbent member has a continuous cell.

3. The fluidic device according to claim 1, wherein:
the liquid-absorbent polymer is a water-absorbent polymer; and
the lyophilic polymer is a water-insoluble hydrophilic polymer.

4. The fluidic device according to claim 1, wherein the liquid-absorbent polymer is dispersed in the lyophilic polymer in the absorbent member.

5. The fluidic device according to claim 4, wherein:
the liquid-absorbent polymer is a water-absorbent polymer; and
the lyophilic polymer is a water-soluble hydrophilic polymer.

6. The fluidic device according to claim 1, wherein the liquid-absorbent polymer is particles having a volume basis average particle diameter of 45 µm or less.

7. The fluidic device according to claim 1, wherein the barrier member has a gas barrier property.

8. The fluidic device according to claim 1, wherein the fluidic device is an immunochromatography device.

9. The fluidic device according to claim 1, wherein the liquid-absorbent polymer is a water-absorbent polymer selected from the group consisting of sodium polyacrylate, cross-linked polyacrylic acid salt, cross-linked vinyl alcohol/acrylic acid salt copolymer, cross-linked polyvinyl alcohol/polymaleic anhydride salt graft copolymer, cross-linked carboxymethyl cellulose salt, and cross-linked starch/acrylic acid salt graft copolymer.

10. The fluidic device according to claim 1, wherein the barrier member is a film or laminate of a material selected from the group consisting of polyethylene wax, polypropylene wax, silicone resin, polycarbonate, and polystyrene.

11. The fluidic device according to claim 1, wherein the hydrophilic porous material of the porous flow path member has a voidage of from 40% to 90%.

12. The fluidic device according to claim 1, wherein the barrier member is of a material selected from the group consisting of waxes, polyamides, and resins.

13. The fluidic device according to claim 1, wherein the barrier member is an elastomer having an elongation rate of 3% or more.

14. The fluidic device according to claim 1, wherein the porous flow path member is made of a hydrophilic porous material comprising a porous a porous portion that is not hydrophobized, and the absorbent member is in physical contact with the porous portion of the flow path member.

15. The fluidic device according to claim 1, further comprising a base member, wherein the flow path member is disposed over the base member.

16. The fluidic device according to claim 1, wherein the barrier member comprises a first opening for introducing an analyte liquid and a second opening through which pressure in the flow path escapes into atmospheric pressure.

* * * * *